(12) United States Patent
McAlister

(10) Patent No.: US 9,416,457 B2
(45) Date of Patent: Aug. 16, 2016

(54) SYSTEM AND METHOD FOR RENEWABLE RESOURCE PRODUCTION, FOR EXAMPLE, HYDROGEN PRODUCTION BY MICROBIAL, ELECTROLYSIS, FERMENTATION, AND/OR PHOTOSYNTHESIS

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 14/519,121

(22) Filed: Oct. 20, 2014

(65) Prior Publication Data
US 2015/0140632 A1    May 21, 2015

Related U.S. Application Data

(60) Division of application No. 13/027,236, filed on Feb. 14, 2011, now Pat. No. 9,040,012, which is a continuation-in-part of application No. 12/806,633, filed on Aug. 16, 2010, now Pat. No. 8,075,750, which (Continued)

(51) Int. Cl.
*C01B 3/02* (2006.01)
*C01B 3/06* (2006.01)

(Continued)

(52) U.S. Cl.
CPC . *C25B 11/03* (2013.01); *C01B 3/24* (2013.01); *C12P 3/00* (2013.01); *C25B 1/02* (2013.01); *C25B 13/02* (2013.01); *C25B 15/00* (2013.01); *C01B 3/02* (2013.01); *C01B 3/06* (2013.01); *C01B 2203/0272* (2013.01);

(Continued)

(58) Field of Classification Search
CPC ........ C25B 11/03; C25B 15/00; C25B 13/02; C01B 3/02; C01B 3/06
See application file for complete search history.

(56) References Cited

U.S. PATENT DOCUMENTS

| 1,771,091 A | 7/1930 | Lawaczeck |
| 3,410,770 A | 11/1968 | Buechler |

(Continued)

FOREIGN PATENT DOCUMENTS

| AT | 346826 | 11/1978 |
| AU | 2122100 | 8/2001 |

(Continued)

OTHER PUBLICATIONS

"Electrifying New Way to Clean Dirty Water." University of Utah, Published: Jan. 5, 2011. Accessed: Jun. 1, 2011. <http://www.unews.utah.edu/old/p/010511-1.html>.

(Continued)

*Primary Examiner* — Wayne Langel
(74) *Attorney, Agent, or Firm* — Perkins Coie LLP

(57) ABSTRACT

System and method for sustainable economic development which includes hydrogen extracted from substances, for example, sea water, industrial waste water, agricultural waste water, sewage, and landfill waste water. The hydrogen extraction is accomplished by thermal dissociation, electrical dissociation, optical dissociation, and magnetic dissociation. The hydrogen extraction further includes operation in conjunction with energy addition from renewable resources, for example, solar, wind, moving water, geothermal, or biomass resources.

17 Claims, 17 Drawing Sheets

Related U.S. Application Data is a continuation-in-part of application No. 12/707,651, filed on Feb. 17, 2010, now Pat. No. 8,075,748, and a continuation-in-part of application No. PCT/US2010/024497, filed on Feb. 17, 2010, and a continuation-in-part of application No. 12/707,653, filed on Feb. 17, 2010, now Pat. No. 8,172,990, and a continuation-in-part of application No. 12/707,656, filed on Feb. 17, 2010, now Pat. No. 8,075,749, and a continuation-in-part of application No. PCT/US2010/024499, filed on Feb. 17, 2010, and a continuation-in-part of application No. PCT/US2010/024498, filed on Feb. 17, 2010.

(60) Provisional application No. 61/304,403, filed on Feb. 13, 2010, provisional application No. 61/237,476, filed on Aug. 27, 2009, provisional application No. 61/153,253, filed on Feb. 17, 2009, provisional application No. 61/345,053, filed on May 14, 2010.

(51) Int. Cl.

| | | |
|---|---|---|
| C02F 3/28 | (2006.01) | |
| C25B 1/02 | (2006.01) | |
| C25B 1/04 | (2006.01) | |
| C25B 11/03 | (2006.01) | |
| C25B 13/02 | (2006.01) | |
| C25B 15/00 | (2006.01) | |
| C01B 3/24 | (2006.01) | |
| C12P 3/00 | (2006.01) | |

(52) U.S. Cl.
CPC .......... *C01B 2203/1235* (2013.01); *C02F 3/28* (2013.01); *C25B 1/04* (2013.01); *Y02P 20/134* (2015.11)

(56) References Cited

U.S. PATENT DOCUMENTS

| | | | |
|---|---|---|---|
| 3,855,386 | A | 12/1974 | Moore |
| 4,019,868 | A | 4/1977 | Sebacher et al. |
| 4,053,576 | A | 10/1977 | Fletcher et al. |
| 4,142,950 | A | 3/1979 | Creamer et al. |
| 4,169,035 | A | 9/1979 | Stummer et al. |
| 4,200,505 | A | 4/1980 | Day et al. |
| 4,243,503 | A | 1/1981 | Lieb et al. |
| 4,282,187 | A | 8/1981 | Corbett et al. |
| 4,339,547 | A | 7/1982 | Corbett et al. |
| 4,341,608 | A | 7/1982 | St. John et al. |
| 4,343,690 | A | 8/1982 | de Nora et al. |
| 4,354,905 | A | 10/1982 | Yoshida et al. |
| 4,377,455 | A | 3/1983 | Kadija et al. |
| 4,391,793 | A | 7/1983 | Boese et al. |
| 4,395,316 | A | 7/1983 | St. John et al. |
| 4,468,311 | A | 8/1984 | de Nora et al. |
| 4,497,112 | A | 2/1985 | Beaver et al. |
| 4,519,342 | A | 5/1985 | Yoon |
| 4,528,270 | A | 7/1985 | Matsunaga et al. |
| 4,548,693 | A | 10/1985 | Kadija et al. |
| 4,568,522 | A | 2/1986 | Corbett |
| 4,574,037 | A | 3/1986 | Samejima et al. |
| 4,896,507 | A | 1/1990 | Hosford et al. |
| 5,015,342 | A | 5/1991 | Ginatta et al. |
| 5,360,522 | A | 11/1994 | Kuroda et al. |
| 5,589,052 | A | 12/1996 | Shimamune et al. |
| 5,660,698 | A | 8/1997 | Scannell et al. |
| 5,711,865 | A | 1/1998 | Caesar et al. |
| 5,779,866 | A | 7/1998 | Tarancon et al. |
| 5,882,382 | A | 3/1999 | Hachisuka et al. |
| 5,904,821 | A | 5/1999 | Blank et al. |
| 6,090,266 | A | 7/2000 | Roychowdhury et al. |
| 6,238,546 | B1 | 5/2001 | Knieper et al. |
| 6,328,863 | B1 | 12/2001 | Wilhelm et al. |
| 6,395,252 | B1 | 5/2002 | Getty et al. |
| 6,446,597 | B1 | 9/2002 | McAlister |
| 6,464,755 | B2 | 10/2002 | Nakanishi et al. |
| 6,471,873 | B1 | 10/2002 | Greenberg et al. |
| 6,495,023 | B1 | 12/2002 | Zeikus et al. |
| 6,525,263 | B2 | 2/2003 | Mueller |
| 6,698,389 | B2 | 3/2004 | Andrews et al. |
| 6,780,306 | B2 | 8/2004 | Schlager et al. |
| 6,802,956 | B2 | 10/2004 | Orlebeke et al. |
| 6,984,305 | B2 * | 1/2006 | McAlister .............. B01D 53/32 205/637 |
| 7,097,748 | B2 | 8/2006 | Duffy et al. |
| 7,138,046 | B2 | 11/2006 | Roychowdhury et al. |
| 7,141,147 | B2 | 11/2006 | Shimamune et al. |
| 7,224,080 | B2 | 5/2007 | Smedstad et al. |
| 7,250,288 | B2 | 7/2007 | Zeikus et al. |
| 7,318,885 | B2 | 1/2008 | Omasa et al. |
| 7,351,316 | B2 | 4/2008 | Yoshida et al. |
| 7,491,453 | B2 | 2/2009 | Liu et al. |
| 7,507,490 | B2 | 3/2009 | Ohtani et al. |
| 7,510,633 | B2 | 3/2009 | Shimko et al. |
| 7,510,640 | B2 | 3/2009 | Gibson et al. |
| 7,645,930 | B2 | 1/2010 | Kelly et al. |
| 7,645,931 | B2 | 1/2010 | Gibson et al. |
| 7,651,602 | B2 | 1/2010 | Helmke et al. |
| 7,674,538 | B2 | 3/2010 | Grieve et al. |
| 7,709,113 | B2 | 5/2010 | Liu et al. |
| 7,762,495 | B2 | 7/2010 | Miller et al. |
| 7,887,679 | B2 | 2/2011 | Kitaori et al. |
| 7,897,022 | B2 | 3/2011 | Thordarsonn et al. |
| 7,922,795 | B2 | 4/2011 | Striemer et al. |
| 7,922,878 | B2 | 4/2011 | Logan |
| 8,075,748 | B2 | 12/2011 | McAlister |
| 8,075,750 | B2 | 12/2011 | McAlister |
| 8,172,990 | B2 | 5/2012 | McAlister |
| 9,040,012 | B2 | 5/2015 | McAlister |
| 2002/0087037 | A1 | 7/2002 | Kaneko et al. |
| 2002/0108866 | A1 | 8/2002 | Bonilla et al. |
| 2002/0110522 | A1 | 8/2002 | Chin et al. |
| 2003/0012985 | A1 | 1/2003 | McAlister |
| 2003/0062270 | A1 | 4/2003 | McAlister |
| 2003/0129469 | A1 | 7/2003 | Sun et al. |
| 2005/0183962 | A1 | 8/2005 | Oakes et al. |
| 2006/0147763 | A1 | 7/2006 | Angenent et al. |
| 2006/0272955 | A1 | 12/2006 | Felder et al. |
| 2006/0272956 | A1 | 12/2006 | Felder et al. |
| 2007/0056842 | A1 | 3/2007 | Roychowdhury et al. |
| 2007/0220887 | A1 | 9/2007 | Monostory et al. |
| 2007/0251830 | A1 | 11/2007 | Conrad et al. |
| 2007/0259216 | A1 | 11/2007 | Logan et al. |
| 2007/0259217 | A1 | 11/2007 | Logan et al. |
| 2007/0274905 | A1 | 11/2007 | Wynn et al. |
| 2008/0047502 | A1 | 2/2008 | Morse et al. |
| 2008/0152967 | A1 | 6/2008 | Roychowdhury et al. |
| 2008/0245660 | A1 | 10/2008 | Little et al. |
| 2008/0245672 | A1 | 10/2008 | Little et al. |
| 2008/0248350 | A1 | 10/2008 | Little et al. |
| 2008/0282882 | A1 | 11/2008 | Saukaitis et al. |
| 2008/0292912 | A1 | 11/2008 | Logan et al. |
| 2008/0311022 | A1 | 12/2008 | Carrington et al. |
| 2009/0007484 | A1 | 1/2009 | Smith et al. |
| 2009/0048354 | A1 | 2/2009 | Bell et al. |
| 2009/0170966 | A1 | 7/2009 | Atkins et al. |
| 2009/0260363 | A1 | 10/2009 | Moriarty et al. |
| 2010/0003184 | A1 | 1/2010 | Nakamura et al. |
| 2010/0107994 | A1 | 5/2010 | Moriarty et al. |
| 2010/0119920 | A1 | 5/2010 | Logan et al. |
| 2010/0151279 | A1 | 6/2010 | Logan et al. |
| 2010/0213050 | A1 | 8/2010 | McAlister et al. |
| 2010/0213052 | A1 | 8/2010 | McAlister |
| 2010/0213076 | A1 | 8/2010 | McAlister et al. |
| 2011/0042203 | A1 | 2/2011 | McAlister et al. |
| 2011/0083971 | A1 | 4/2011 | Roychowdhury et al. |

FOREIGN PATENT DOCUMENTS

| | | |
|---|---|---|
| AU | 2005248951 | 2/2006 |
| AU | 2007248040 | 11/2007 |
| BR | 017078 | 11/2002 |

(56) References Cited

FOREIGN PATENT DOCUMENTS

| | | |
|---|---|---|
| CA | 2154465 | 8/1994 |
| CA | 2399400 | 8/2001 |
| CA | 2650818 | 11/2007 |
| CN | 1243669 | 2/2000 |
| CN | 1437564 | 8/2003 |
| CN | 101485029 | 7/2009 |
| DE | 60032179 | 1/2007 |
| EP | 1263686 | 12/2002 |
| EP | 1939968 | 7/2008 |
| EP | 2025033 | 2/2009 |
| ES | 2275490 | 6/2007 |
| FR | 2286891 | 4/1976 |
| JP | 2003521258 | 7/2003 |
| JP | 2004307878 | 11/2004 |
| KR | 100808736 | 2/2008 |
| KR | 101218952 | 1/2013 |
| MX | PA02007361 | 9/2004 |
| WO | 0156938 | 8/2001 |
| WO | 03042430 | 5/2003 |
| WO | 2004094698 | 11/2004 |
| WO | 2006010149 | 1/2006 |
| WO | 2006130557 | 12/2006 |
| WO | 2007039661 | 4/2007 |
| WO | 2007131022 | 11/2007 |
| WO | 2007131029 | 11/2007 |
| WO | 2008036347 | 3/2008 |
| WO | 2008124538 | 10/2008 |
| WO | 2009003006 | 12/2008 |
| WO | 2010013244 | 2/2010 |

OTHER PUBLICATIONS

"INOTEC—Cutting-Edge Wastewater Treatment." Accessed: Jan. 31, 2011. <http://www.inotec.us/>. pp. 1-3.
"New Electrolytic Cells to Play a Role in Tomorrow's Local Energy Supply." Science Blog. Published: Apr. 27, 2010. Accessed: Jun. 1, 2011. <http://scienceblog.com/33189/new-electrolytic-cells-to-play-a-role-in-tomorrows-local-energy-supply/>. pp. 1-5.
"Utah Microbubbles Clean Dirty Soil in China." University of Utah, Published: Oct. 13, 2010. Accessed: May 27, 2011. <http://unews.utah.edu/old/p/101110-1.html>. pp. 1-2.
Bioremediation and Bioprocess Consulting LLC, "Biocapsules Time-Release of Microbes and/or Nutrients." Inotec.com; Published: 2003. Accessed: Jan. 31, 2011. 1 page.
Chen et al., "Parylene-Encapsulated Copolymeric Membranes as Localized and Sustained Drug Delivery Platforms." Annals of Biomedical Engineering, vol. 37, Issue 10 (Oct. 2009): pp. 2003-2017.
European Search Report for EP 12167100.2 filed on Feb. 17, 2010 based on PCT/US2010/096504; Date of Mailing: Oct. 31, 2012, 8 pages.
Examiner's Report issued for Canadian National Phase Application No. 2,752,698 based on PCT/US10/24499, Date of Filing of Application: Feb. 17, 2010, Date of Mailing: Jul. 31, 2012, 3 pages.
Final Office Action for U.S. Appl. No. 12/806,633; Applicant: McAlister Technologies, LLC; Date of Mailing: Aug. 5, 2011; 7 pages.
International Search Report and Written Opinion for Application No. PCT/US2010/002259; Applicant: McAlister Technologies, LLC; Date of Mailing: May 2, 2011; 9 pages.
International Search Report and Written Opinion for Application No. PCT/US2010/024498; Applicant: McAlister Technologies, LLC; Date of Mailing: Apr. 23, 2010; 7 pages.
International Search Report and Written Opinion for Application No. PCT/US2010/024816; Applicant: McAlister Technologies, LLC; Date of Mailing: Feb. 24, 2012; 15 pages.
International Search Report and Written Opinion for Application No. PCT/US2010/24497; Applicant: McAlister Technologies, LLC; Date of Mailing: Apr. 12, 2010; pp. 1-14.
International Search Report and Written Opinion for Application No. PCT/US2010/24499; Applicant: McAlister Technologies, LLC; Date of Mailing: Apr. 21, 2010; 9 pages.
Non-Final Office Action for U.S. Appl. No. 12/707,651; Applicant: McAlister Technologies, LLC; Date of Mailing: Mar. 23, 2011; 12 pages.
Non-Final Office Action for U.S. Appl. No. 12/707,653; Applicant: McAlister Technologies, LLC; Date of Mailing: Apr. 11, 2011; 12 pages.
Non-Final Office Action for U.S. Appl. No. 12/707,656; Applicant: McAlister Technologies, LLC; Date of Mailing: Mar. 29, 2011; 8 pages.
Non-Final Office Action for U.S. Appl. No. 12/806,633; Applicant: McAlister Technologies, LLC; Date of Mailing: Mar. 31, 2011; 14 pages.
Non-Final Office Action for U.S. Appl. No. 13/168,817; Applicant: McAlister Technologies, LLC; Date of Mailing: Sep. 19, 2011; 6 pages.
Office Action issued for Japanese National Phase Application No. 2011-551196 based on PCT/USUS10/24496, Date of Filing of Application: Feb. 17, 2010, Date of Mailing: Aug. 27, 2012, 4 pages.
Office Action issued for Japanese National Phase Application No. 2011-551197 based on PCT/USUS10/24497, Date of Filing of Application: Feb. 17, 2010, Date of Mailing: Aug. 27, 2012, 3 pages.
Office Action issued for Japanese National Phase Application No. 2011-551198 based on PCT/USUS10/24498, Date of Filing of Application: Feb. 17, 2010, Date of Mailing: Aug. 27, 2012, 2 pages.
Rozendal et al., "Principle and Perspectives of Hydrogen Production Through Biocatalyzed Electrolysis," International Journal of Hydrogen Energy, Elsevier Science Publishers B.V., Barking, GB, vol. 31, No. 12, Sep. 1, 2006, pp. 1632-1640.
Supplementary European Search Report for EP 10744269.1 filed on Feb. 17, 2010 based on PCT/US2010/024497; Date of Mailing: Oct. 31, 2012, 6 pages.
Supplementary European Search Report for EP 10744271.7 filed on Feb. 17, 2010 based on PCT/US2010/024499; Date of Mailing: Oct. 31, 2012, 22 pages.
Yagi et al., "A New Method for Hydrogenase Based on an Enzymic Electrode Reaction," J. Biochem., 78, 1975, pp. 443-454.
Yagi, "Separation of Hydrogenase-Catalyzed Hydrogen-Evolution System From Electron-Donating System by Means of Enzymic Electric Cell Technique," Proc, Natl. Acad. Sci. USA, vol. 73, No. 9, Sep. 1976, pp. 2947-2949.
"U of U Scientists Electrify Microbes to Clean Dirty Water." Water and Wastewater.Com, Water Treatment Equipment Homepage. Published: Jan. 18, 2011. Accessed: May 27, 2011. <http://www.waterandwastewater.com/www_services/news_center/publish/industry_news/U_o_, f_U_Scientists_Electrify_Microbes_to_Clean_Dirty_Water_printer.shtml>. pp. 1-2.
McConnell et al., "A Hybrid Solar Concentrator for the Electrolytic Production of Hydrogen." U.S.Department of Energy, National Renewable Energy Laboratory, Howard University; Published: Dec. 12, 2005. Web. Accessed: Jun. 8, 2011. <http://www1.eere.energy.go,v/solar/pdfs/mcconnell.pdf>. pp. 1-23.

* cited by examiner

SYSTEM AND METHOD FOR RENEWABLE RESOURCE PRODUCTION, FOR EXAMPLE, HYDROGEN PRODUCTION BY MICROBIAL, ELECTROLYSIS, FERMENTATION, AND/OR PHOTOSYNTHESIS

CROSS-REFERENCE TO RELATED APPLICATIONS

The present application claims priority to and the benefit of U.S. Patent Application No. 61/304,403, filed on Feb. 13, 2010 and titled FULL SPECTRUM ENERGY AND RESOURCE INDEPENDENCE, and U.S. Patent Application No. 61/345,053, filed on May 14, 2010 and titled SYSTEM AND METHOD FOR RENEWABLE RESOURCE PRODUCTION. The present application is a continuation in part of U.S. patent application Ser. No. 12/806,633, filed on Aug. 16, 2010 and titled ELECTROLYTIC CELL AND METHOD OF USE THEREOF which claims priority to and the benefit of U.S. Provisional Application No. 61/304,403, filed Feb. 13, 2010 and titled FULL SPECTRUM ENERGY AND RESOURCE INDEPENDENCE and is a continuation-in-part of U.S. patent application Ser. No. 12/707,651, filed Feb. 17, 2010 and titled ELECTROLYTIC CELL AND METHOD OF USE THEREOF; PCT Application No. PCT/US10/24497, filed Feb. 17, 2010 and titled ELECTROLYTIC CELL AND METHOD OF USE THEREOF; U.S. patent application Ser. No. 12/707,653, filed Feb. 17, 2010 and titled APPARATUS AND METHOD FOR CONTROLLING NUCLEATION DURING ELECTROLYSIS; PCT Application No. PCT/US10/24498, filed Feb. 17, 2010 and titled APPARATUS AND METHOD FOR CONTROLLING NUCLEATION DURING ELECTROLYSIS; U.S. patent application Ser. No. 12/707,656, filed Feb. 17, 2010 and titled APPARATUS AND METHOD FOR GAS CAPTURE DURING ELECTROLYSIS; and PCT Application No. PCT/US10/24499, filed Feb. 17, 2010 and titled APPARATUS AND METHOD FOR CONTROLLING NUCLEATION DURING ELECTROLYSIS; each of which claims priority to and the benefit of the following applications: U.S. Provisional Patent Application No. 61/153,253, filed Feb. 17, 2009 and titled FULL SPECTRUM ENERGY; U.S. Provisional Patent Application No. 61/237,476, filed Aug. 27, 2009 and titled ELECTROLYZER AND ENERGY INDEPENDENCE TECHNOLOGIES; U.S. Provisional Application No. 61/304,403, filed Feb. 13, 2010 and titled FULL SPECTRUM ENERGY AND RESOURCE INDEPENDENCE. Each of these applications is incorporated herein by reference in its entirety. To the extent the foregoing application and/or any other materials incorporated herein by reference conflict with the disclosure presented herein, the disclosure herein controls.

BACKGROUND

Our economy for supporting 7 billion persons depends upon annually mining and burning fossil resources that took over one million years to accumulate. In addition to being temporary, our economy causes expensive harm to the environment and illnesses that are caused by air and water pollution cause loss of productivity of the human workforce.

Renewable resources such as solar, wind, wave, falling water and biomass wastes have tremendous potential but have not been utilized to any significant extent because of difficult materials problems and inadequate designs failed to overcome these problems.

For example, renewable resources for producing electricity are often intermittent. Solar energy is a daytime event and the daytime solar-energy-concentration potential varies seasonally. Wind energy is highly variable. Falling water varies seasonally and is subject to extended drought. Biomass is seasonally variant and subject to droughts. Dwellings have greatly varying demands including daily, seasonal, and occasional energy consumption rates. Throughout the world, energy that could be delivered by hydroelectric plants, wind farms, biomass conversion and solar collectors is neglected or wasted because of the lack of a practical way to save energy or electricity until it is needed. Demand by a growing world population for energy has grown to the point of requiring more oil and other fossil resources than can be produced. Cities suffer from smog and global climate changes caused by the combustion of fossil fuels.

Also, burgeoning demands have developed for hydrogen, oxygen, carbon, and other products that can be provided by thermochemistry or electrolytic dissociation of feedstocks such as water, biomass wastes, or organic acids derived from biowaste. For example, the global market for hydrogen is more than $40 billion, and includes ammonia production, refineries, chemical manufacturing and food processing.

Electro-chemical production of fuels, metals, non-metals, and other valuable chemicals has been limited by expensive electricity, low electrolyzer efficiency, high maintenance costs, and cumbersome requirements for energy intensive operations such as compressive pumping of produced gases to desired transmission, storage, and application pressures. Efforts to provide technology for reducing these problems are noted and incorporated hereby in publications such as "Hydrogen Production From Water By Means of Chemical Cycles," by Glandt, Eduardo D., and Myers, Allan L., Department of Chemical and Biochemical Engineering, University of Pennsylvania, Philadelphia, Pa. 19174; Industrial Engineering Chemical Process Development, Vol. 15, No. 1, 1976; "Hydrogen As A Future Fuel, by Gregory, D. P., Institute of Gas Technology; and "Adsorption Science and Technology": Proceedings of the Second Pacific Basin Conference on Adsorption Science and Technology:Brisbane, Australia, 14-18 May 2000, By D. Do Duong, Duong D. Do, Contributor Duong D. Do, Published by World Scientific, 2000; ISBN 9810242638, 9789810242633.

Electrolyzers that allow hydrogen to mix with oxygen present the potential hazard of spontaneous fire or explosion. Efforts including low and high pressure electrolyzers that utilize expensive semi-permeable membrane separation of the gas production electrodes fail to provide cost-effective production of hydrogen and are prone to degradation and failure due to poisoning by impurities. Even in instances that membrane separation is utilized, the potential danger exists for membrane rupture and fire or explosion due to mixing of high-pressure oxygen and hydrogen.

Some commercial electrolyzers use expensive porous electrodes such as an electrolytic proton exchange membrane (PEM) that only conducts hydrogen ions. (See Proton Energy Company and the Electrolyzer Company of Canada.) This limits the electrode efficiency because of polarization losses, gas accumulation, and reduction of available electrode area for the dissociation of water that can reach the interface of the electrodes and PEM electrolyte. Along with the limited electrode efficiency are other difficult problems including membrane ruptures due to the pressure difference between the oxygen and hydrogen outlets, membrane poisoning due to impurities in the make-up water, irreversible membrane degradation due to contaminants or slight overheating of the membrane, membrane degradation or rupture if the membrane is allowed to dry out while not in service, and degradation of electrodes at the membrane interface due to corrosion by one or more inducements such as concentration cell formation, galvanic cells between catalysts and bulk electrode material, and ground loops. Layering of electrode and PEM materials provide built in stagnation of the reactants or products of the reaction to cause inefficient operation. PEM electrochemical cells require expensive membrane material, surfactants, and catalysts. PEM cells are easily poisoned, overheated, flooded or dried out and pose operational hazards due to membrane leakage or rupture.

In addition to inefficiencies, problems with such systems include parasitic losses, expensive electrodes or catalysts and membranes, low energy conversion efficiency, expensive maintenance, and high operating costs. Compressors or more expensive membrane systems are situationally required to pressurize hydrogen and oxygen and other products of electrolysis. Corollaries of the last mentioned problem are unacceptable maintenance requirements, high repair expenses, and substantial decommissioning costs.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the various elements as drawn, are not intended to convey any information regarding the actual shape of the particular elements, and have been solely selected for ease of recognition in the drawings.

DETAILED DESCRIPTION

Figure 1:
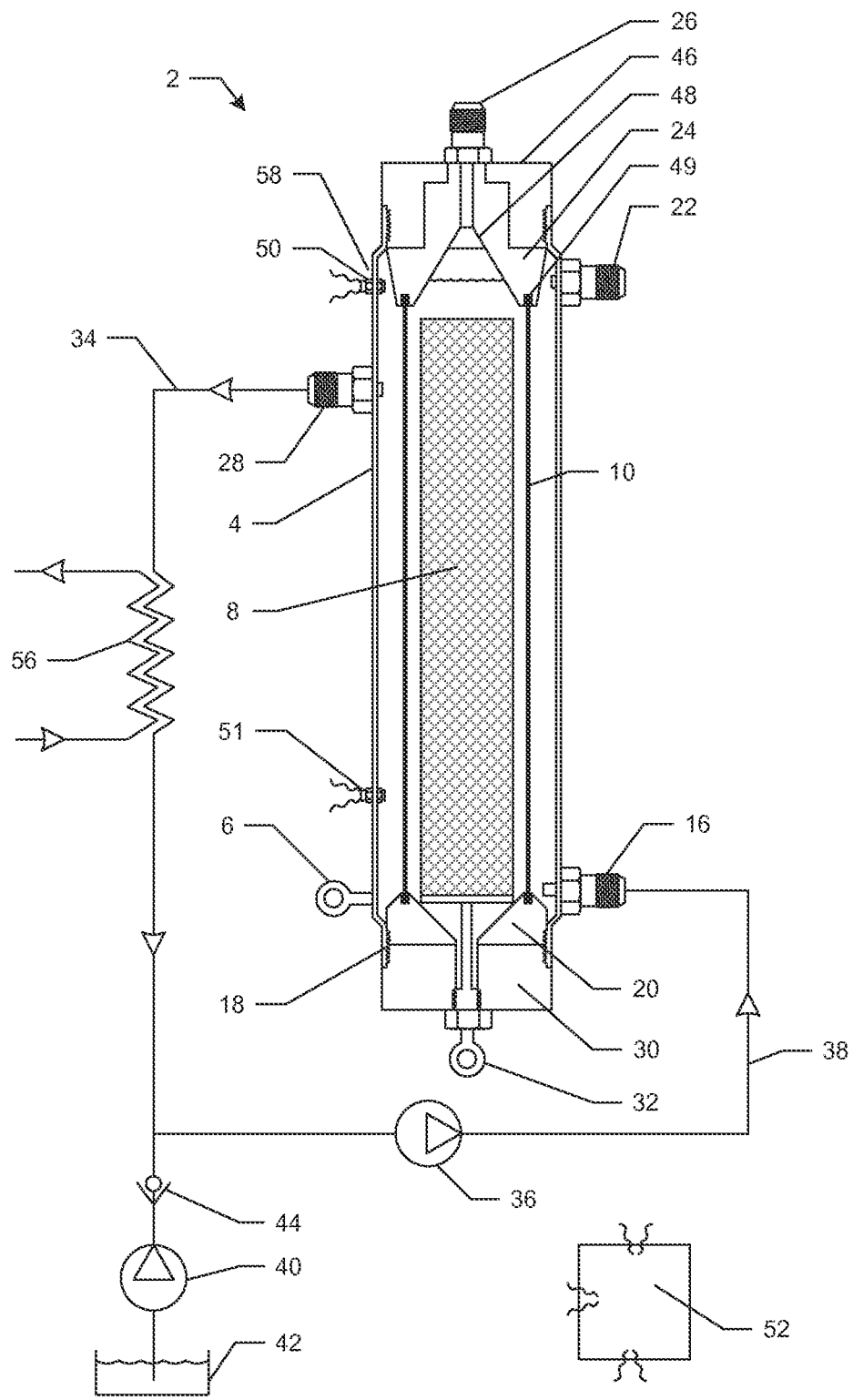
FIG. 1 shows an electrolytic cell in accordance with aspects of the disclosure.

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with solar concentrators or electrolytic cells have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, which is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

Similar subject matter is described in commonly assigned U.S. patent application Ser. No. 61/178,442, filed May 14, 2009, and entitled "Energy Independence Technologies". Much of the detailed description provided herein is disclosed in the provisional patent application; other additional material will be recognized by those skilled in the relevant art as being inherent in the detailed description provided in such provisional patent application or well known to those skilled in the relevant art based on the detailed description provided in the provisional patent application.

The headings provided herein are for convenience only and do not interpret the scope or meaning of the claimed invention.

1. Electrolytic Cell

In one embodiment, an electrolytic cell and method of use is provided. While the electrolytic cell may be used in many applications, it is described in this embodiment for use in the production of hydrogen and oxygen. An electrolytic cell according to the present embodiment provides for reversible separated production of pressurized hydrogen and oxygen and tolerates impurities and products of operation. The embodiment further provides the option for operating an electrolysis process which comprises the steps of supplying a substance to be dissociated that is pressurized to a much lower magnitude than desired for compact storage, applying an electromotive force between electrodes to produce fluid products that have less density than the substance that is dissociated and restricting expansion of the less dense fluid products until the desired pressure for compact storage is achieved. This and other embodiments can improve the energy utilization efficiency of dwellings such as homes, restaurants, hotels, hospitals, canneries, and other business facilities by operation of heat engines or fuel cells and to utilize heat from such sources to cook food, sterilize water and deliver heat to other substances, provide space heating or to facilitate anaerobic or electrically induced releases of fuel for such engines or fuel cells. Moreover, one skilled in the art will appreciate that aspects of the embodiments disclosed herein can apply to other types of electrochemical cells to provide similar advantages.

Contrary to conventional electrochemical electrodes which depend largely upon relatively slow diffusion, convection, and concentration gradient processes to produce mass transport and/or deliver ions for production of desired constituents, the present embodiment provides more efficient mass transport including rapid ion replenishment processes and deliveries to desired electrodes by pumping actions of low-density gases escaping from a denser liquid medium as described herein. This assures greater electrical efficiency, more rapid dissociation, and greater separation efficiency along with prevention of undesirable side reactions. Increasing the rate and efficiency of ion production and delivery to electrodes increases the system efficiency and current limit per electrode area.

Referring to FIG. 1, an electrolytic cell 2 in which a container 4 such as a metallic tube serves as a containment vessel is shown. Optionally, the container 4 may also serve as an electrode as shown in FIG. 1. A porous electrode such as cylindrical conductive wire screen electrode 8 is coaxially located and separated from tubular electrode 4 by an electrolytic inventory of liquid such as an acid or base. Liquid electrolyte occupies the interior space of container 4 to the liquid-gas interface in insulator 24. A layer of plated, plasma sprayed, or composited electrode material on a dielectric sleeve or a conductive cylindrical inner liner electrode 4' (not shown) may be provided within container 4 to serve as an electrically separated element of the assembly to enable convenient replacement as a maintenance item or to serve as one of a number of segmented electrode elements for purposes of optional polarity, and/or in series, parallel, or series-parallel connections. In the present reversible embodiment for the electrolysis of water, electrode 8 may be considered the electron source or cathode such that hydrogen is produced at electrode 8, and electrode 4 may be considered the anode such that oxygen is produced at electrode 4. Container 4 may be capable of pressurization. Pressurization of the contents of container 4 is restrained by sealed caps 30 and 46. Support, electrical insulation, and stabilization of components including electrode 8, gas separator 10, and electrical connection 32 are provided by dielectric insulator bodies 20 and 24 as shown. Pressurization of the electrolytic cell 2 can be accomplished by self-pressurization due the production of gas(es) during electrolysis, by an external source such as a pump or by any combination thereof.

Separator 10 is configured to be liquid permeable but to substantially prevent gas flow or transport from the cathode side of the separator to the anode side of the separator and vice versa, include substantially preventing the flow of gas dissolved in the electrolyte or after nucleation of gas bubbles. Optionally, electrode 8 may be configured to act as separator 10 such that a distinct separator is not necessary. Alternatively, separator 10 may include the electrode 8 or electrode 8 may include separator 10. In addition, separator 10 may also include the anodic electrode 4 or anodic electrode 4 may include separator 10.

Insulator 24 is shaped as shown and as needed to separate, collect and/or extract gases produced by electrodes such as 4 and 8 including utilization in combination with separator 10. In the concentric cylindrical geometry shown, insulator 24 has a central conical cavity within which gases released on electrode 8 are collected. Concentrically surrounding this central cavity is an annular zone that collects the gases released from the surfaces of electrode 4' or from the inside of container electrode 4.

Optionally, a catalytic filter 48 may be placed in the upper collection passage of 24 as shown. Oxygen that manages to reach catalytic filter 48 including travel by crossing separator 10 can be catalytically induced to form water by reacting with hydrogen, which may then return to the electrolyte. The vast excess of hydrogen can serve as a heat sink to prohibit the heat released by this catalytic reaction from affecting the electrolytic cell. Purified hydrogen is supplied at fitting 26 as shown. Similarly it may be preferred to provide a catalytic filter 49 in the upper region of the circumferential annulus that collects oxygen as shown, for converting any hydrogen that reaches the oxygen annulus into water. Oxygen is removed at fitting 22 as shown. Alternatively, the catalytic filters may be placed at, near or inside fittings 22 and 26.

In illustrative operation, if water is the substance to be dissociated into hydrogen and oxygen, a suitable electrolyte is prepared such as an aqueous solution of sodium bicarbonate, sodium caustic, potassium hydroxide, or sulfuric acid and is maintained at the desired level as shown by sensor 50 that detects the liquid presence and signals controller 52 to operate pump 40 to add water from a suitable source such as reservoir 42 as needed to produce or maintain the desired inventory or pressure. Controller 52 is thus responsive to temperature or pressure control sensor 58 which may be incorporated in an integrated unit with liquid level sensor 50 or, liquid inventory sensor 51 and control pumps 36 and 40 along with heat exchanger 56 which may include a circulation pump of a system such as a radiator or heater (not shown) to receive or deliver heat. Similarly, a heating or cooling fan maybe utilized in conjunction with such operations to enhance receipt or rejection of heat from sources associated with the electrolytic cell 2.

In some embodiments where the electrolytic cell 2 is to be applied cyclically, e.g., when surplus electricity is inexpensive and not otherwise demanded, electrolytic cell 2 can be operated with considerable variation of the water inventory. At times that surplus electricity is not available or it is turned off, hydrogen and oxygen supplies may be extracted from container 4 and the system is allowed to return to ambient pressure. Ambient pressure water can then be added to fully load the system, which can be provided to have a large annular volume around the circumference of insulator 24 as may be desired to facilitate such cyclic low-pressure filling and electrolysis operations to deliver hydrogen or oxygen at the desired high pressure needed for pressure or chemical energy to work conversions, compact storage, and provide rapid transfers to vehicles, tools, or appliance receivers.

Upon application of current and generation of voluminous gaseous supplies of hydrogen and oxygen from a much smaller inventory of liquid, the system may be pressurized as desired and remains pressurized until the inventory of water in solution is depleted to the point of detection by sensors 50 or 51 which enables controller 52 to either interrupt the electrolysis cycle or to add water by pressure pump 40 from reservoir 42 as shown. It may be preferable to add water across a valve such as check valve 44 as shown to allow multiple duties or maintenance on pump 40 as needed.

Figure 2:
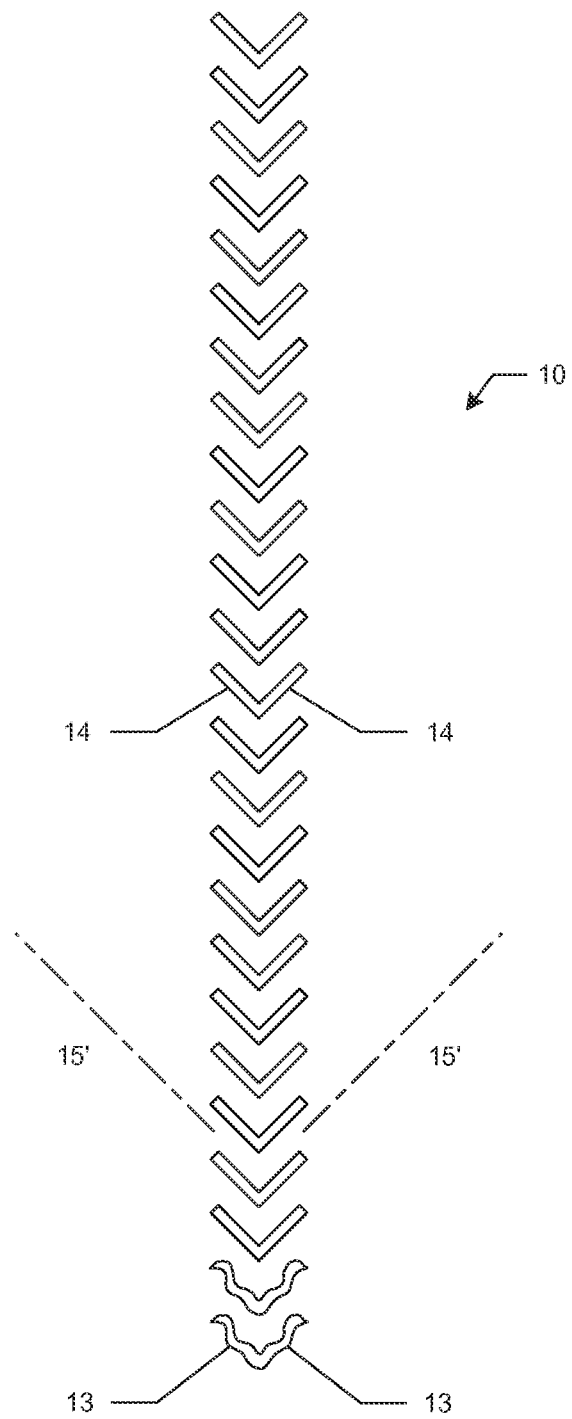
FIG. 2 shows a magnified view of a portion of the embodiment of FIG. 1 in accordance with aspects of the disclosure.
Figure 3:
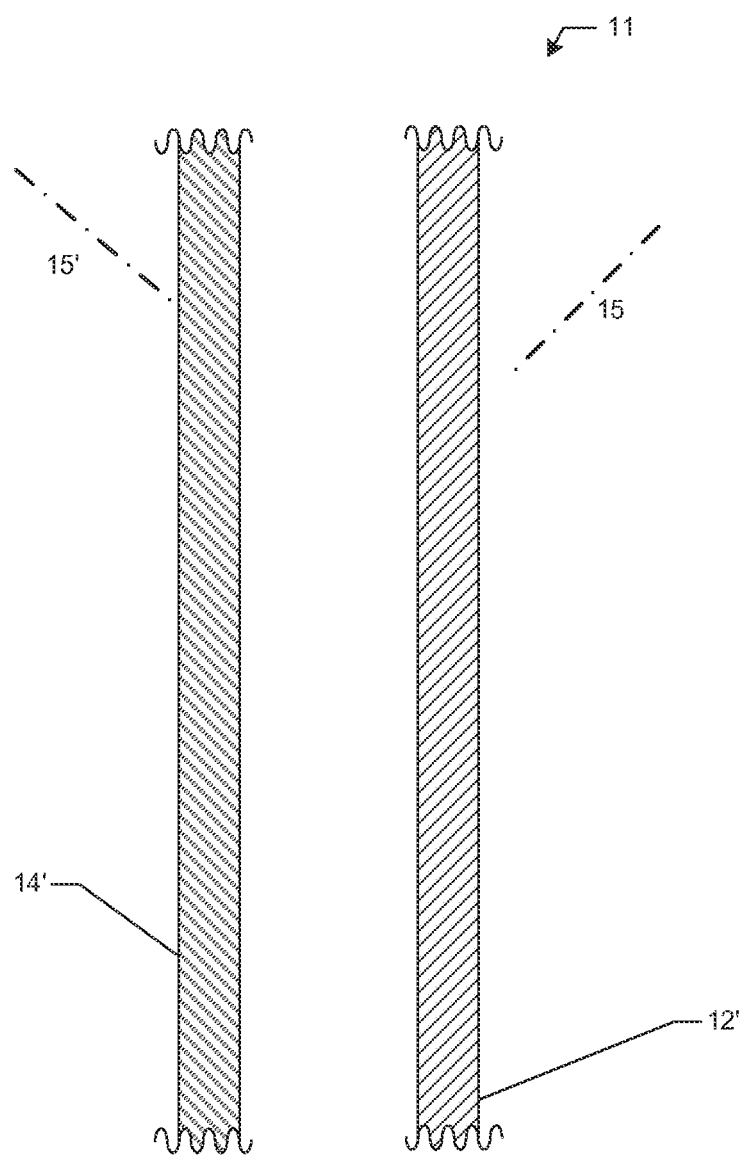
FIG. 3 shows a variation of the embodiment of FIG. 2 in accordance with aspects of the disclosure.

Referring to FIGS. 1, 2 and 3, FIG. 2 shows one embodiment of the separator 10 of FIG. 1 in which the separator includes two inclined surfaces 14 forming a "V" shape. If the electrolyte is water based, electrons are added to porous electrode 8 such as a woven wire cylinder through connection 32 and are removed from container 4 through electrical connection 6 to continuously convert hydrogen ions into hydrogen atoms and subsequently diatomic molecules that can nucleate to form bubbles on or near electrode 8. Hydrogen and oxygen bubbles are typically much less dense than water based electrolytes and are buoyantly propelled upward. Oxygen bubbles are similarly propelled upward and separated from hydrogen by the geometry of coaxial separator 10 as shown in the magnified section view of FIG. 2. The configuration shown in FIG. 2 may be used in any application in which the flow of gas formed during operation of the electrolytic cell 2 is desirable. Further, said separator configuration may be employed in other configurations of electrochemical cells known in the art. Alternatively, if the materials formed during electrolysis is of a higher density than the electrolyte, separator 10 may be inverted forming a "A" shape. Similarly if one material formed at the cathode by electrolysis is less dense than the electrolyte and another material formed at the anode is more dense that the electrolyte, separator 10 may be comprised of a slanted "/" or "\" shapes to deflect the less dense material away from the more dense material.

Mixing of hydrogen with oxygen that is released from 4' or the inside of container 4 is prevented by a liquid-permeable barrier, separator 10 which efficiently separates gases by deflection from the surfaces 12' and 14 which are inclined against oxygen and hydrogen entry, flow, or transmission as shown. Alternatively, separator 10 may include a helical spiral that is composed of an electrically isolated conductor or from inert dielectric material such as 30% glass filled ethylene-chlorotrifluoroethylene in which the cross section of the spiraled strip material is in a "V" configuration as shown to serve as an electrical insulator and gas separator.

Passageways for fluid travel can be increased as desired to meet fluid circulation and distribution needs by corrugating the strip occasionally or continuously particularly at each edge to produce clearance between each layer of the helix, or alternatively at the stack of formed disks that make up the section shown in FIG. 2 as a magnified corrugations as shown at 13 in section view. It is generally advantageous to have each of such corrugations undulate about an appropriately inclined radial axis more or less as shown with respect to axis 15 and 15'. This allows the overall liquid-porous but gas-barrier wall thickness of separator 10 that is formed to be a desired thickness, for example, about 0.2 mm (0.008") thick or less.

Separator 10 may be of any suitable dimensions including very small dimensions and with respect to surface energy conditions sufficient to allow the liquid electrolyte to pass toward or away from electrode 8 while not allowing passage of gases because of the buoyant propulsion and upward travel of the gas. An alternative embodiment applicable in, for example, relatively small fuel cells and electrolyzers, is provided by a multitude of closely-spaced flattened threads with the cross section shown in FIG. 2 in which such threads are woven or adhered to threads that provide mostly open access of liquids and are disposed in the mostly vertical direction on one or both sides of the "V" shaped threads. This allows the overall liquid-porous but gas-barrier wall thickness of separator 10 that is formed to be about 0.1 mm (0.004") thick or less.

Upward buoyant propulsion deflects gas bubble collisions on the inclined surfaces 12 and 14. This feature overcomes the difficulties and problems of the prior art conventional approaches that cause inefficiencies due to one or more of electrical resistance, fouling, stagnation, corrosion, and polarization losses. Moreover, some configurations can promote electrolyte circulation in concentric layers due to the buoyant pumping action of rising bubbles that produces flow of electrolyte upward and, as the gas(es) escape at the top of the liquid, the relatively gas-free and denser electrolyte flows toward the bottom as it is recycled to replace the less dense electrolyte mixed with bubbles or including dissolved gas. A heat exchanger 56 may be operated as needed to add or remove heat from electrolyte that is circulated from the top of container 4 to the bottom as shown. Pump 36 may be used as needed to increase the rate of electrolyte circulation or in conjunction with pump 40 to add make up water.

In some embodiments high current densities are applied, including systems with rapid additions of organic material. In such embodiments, it may be advantageous to circulate the electrolyte with pump 36 which returns relatively gas free electrolyte through fitting 28 through line 34 to pump 36 to return to container 4 through line 38 and fitting 16 as shown. It may be preferred to enter returning electrolyte tangentially at fitting 16 to produce a swirling delivery that continues to swirl and thus synergistically enhances the separation including the action by separator 10 that may be utilized as described above. Depending upon the pressure of operation, hydrogen is about fourteen times less dense and more buoyant than the oxygen and tends to be readily directed at higher upward velocity by separator 10 for pressurized collection through filter 48 at fitting 26. At very high current densities and in instances that electrolytic cell 2 is subjected to tilting or G-forces as might be encountered in transportation applications, the velocity of electrolyte travel is increased by pump 36 to enhance swirl separation and thus prevents gases produced on an anode from mixing with gases produced by a cathode.

Some embodiments of non-conductive gas barrier and liquid transmitting embodiments including separator 10 enable much less expensive and far more rugged and efficient reversible electrolyzers to be manufactured than previous approaches including those that depend upon proton exchange membranes to separate gases such as hydrogen and oxygen. In one aspect, separator 10 can be designed to improve electrolyte flow during electrolysis. For example, separator 10 can be configured to promote the spiral flow of ions in liquid electrolyte inventories traveling upward from port 16 to port 28. This assures that each portion of the electrodes receives freshly replenished ion densities as needed for maximum electrical efficiency. Such electrode washing action can also rapidly remove bubbles of hydrogen and oxygen as they form on the respective electrodes of the electrochemical cell.

FIG. 3 shows the edge view of representative portions of component sheets or helical strips of another aspect of separator 10 for providing electrical isolation adjacent electrodes including flat plate and concentric electrode structures while achieving gas species separation as described above. In assembly 11, sheets 12' and 14' form a cross section that resembles and serves functionally as that of separator 10. Flat conductive or non-conductive polymer sheet 12' is prepared with multitudes of small holes on parallel centerlines that are inclined to form substantial angles such as shown by first angle 15 of approximately 35° to 70° angles with the long axis of sheet 12' as shown. Polymer sheet 14' is similarly prepared with multitudes of small holes on parallel centerlines that are substantially inclined as shown by second angle 15' to form approximately 35° to 70° angles with the long axis of sheet 14' as shown.

In other embodiments the angles 15 and 15' can be varied depending on the material to be separated during the electrolysis process. For example the angles could be declined, for electrolysis of compounds that have no gaseous constituent or only one gaseous constituent. If a compound such as Al2O3 is dissociated by electrolysis in cryolite-alumina electrolyte to form aluminum and oxygen, the aluminum is more dense than the cryolite-alumina electrolyte and the aluminum separating cathode electrode or associated separator would be configured (by, e.g., declined angles) to send the aluminum downward and away from the oxygen traveling upward.

Figure 4:
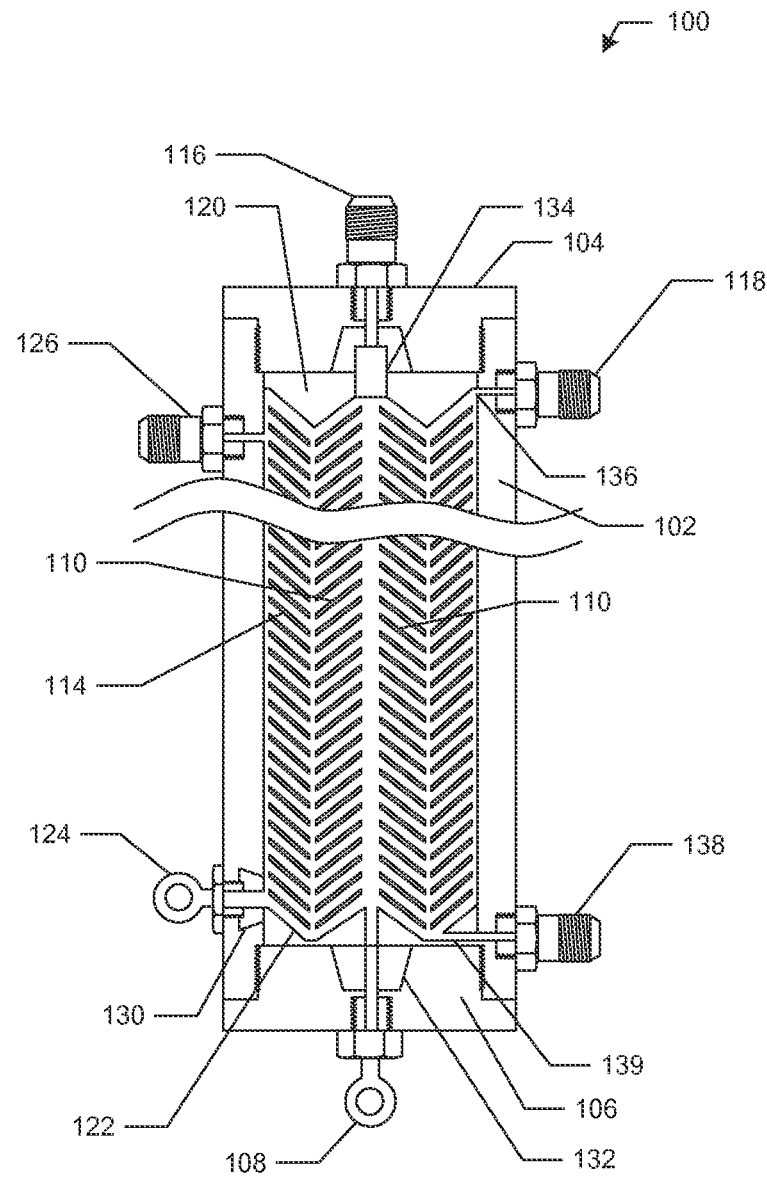
FIG. 4 shows an electrolytic cell in accordance with aspects of the disclosure.

Multitudes of such small holes with diameters of about 1/12 to 1/3 of the sheet thickness dimension can readily be made in sheets 12' and 14' by suitable technologies including laser drilling, hot needle piercing, or by high-speed particle penetrations. Sheets 12' and 14' each of which are typically about 0.025 to 0.25 mm (0.001" to 0.10") thick can be held together by welding or otherwise bonding, thread ties, elastic bands, or one or more spiral wraps of conductive or nonconductive wire on the resulting outside diameter to form as an assembly with electrode 8. Sheets 12' and 14' may also be joined occasionally or continuously by adhesives or by thermal or solvent fusion. Thus, where the inclined holes of sheet 12' overlap the holes of sheet 14' passageways are formed to enable liquid and/or electrolyte travel while prohibiting gas transmission through the gas barrier membrane that is formed. Referring to FIGS. 1 and 4, tubular constructions of the assembled gas barrier sheets may be formed with the appropriate diameter for embodiments 2 or 100 by adhering or welding the butt seam or by providing an overlapped seam that performs as the intended separation gas barrier.

For electrolysis of water, a variety of electrolytes are suitable. In one embodiment potassium hydroxide may be used with low carbon steel for the containment vessel 4. Extended life with increased corrosion resistance may be provided by nickel plating cylinder 4 or by utilization of a suitable stainless steel alloy. In other aspects, increased containment capacity can be provided by overwrapping cylinder 4 with high-strength reinforcement such as glass, ceramic, or carbon filaments or a combination thereof.

Depending upon the particular application and strength requirements it may be advantageous to use about 30% glass filled ethylene chlorotrifluoro-ethylene for insulating separators 20 and 24. Electrode 8 may be made of woven nickel or type 316 stainless steel wires. Separator 10 may be made from about 30% glass filled ethylene-chlorotrifluoro-ethylene strip.

In another embodiment, it is also intended to utilize controlled applications of electricity to produce methane or hydrogen separately or in preferred mixtures from organic electrolytes. In some aspects, the embodiment can operate in conjunction with the embodiments of co-pending patent application including Ser. No. 09/969,860, which is incorporated herein by reference. Anaerobic digestion processes of organic materials that ordinarily produce methane can be controlled to produce an electrolyte that releases hydrogen at considerably lower voltage or by a reduced on-time of a pulse-width modulated duty cycle and resulting electricity expenditure than that required to dissociate water.

Acidity or pH of the organic solution that is produced by microbial digestion can be maintained by a natural bicarbonate buffered interaction. The bicarbonate buffer may be supplemented by co-production of carbon dioxide in the digestion process. The process may be generalized for various steps in anaerobic digestion processes of organic compounds by illustrative digestion of a simple carbohydrate or glucose that may have many competing and complementary process steps such as:

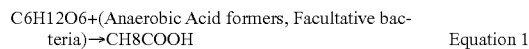

C6H12O6+(Anaerobic Acid formers, Facultative bacteria)→CH8COOH    Equation 1

CH8COOH+NH4HC6O3→CH8COONH4+H2O+CO2    Equation 2

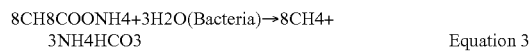

8CH8COONH4+3H2O(Bacteria)→8CH4+3NH4HCO3    Equation 3

In instances that methane from such solutions is desired, pH control near 7.0 may be needed. At ambient pressure, pH of about 7.0, and 35-37° C. (99° F.), methanogenesis is favored. Most domestic wastewater contains biowastes with both macro and micronutrients required by the organisms that provide methanogenesis. Maintaining relatively large concentrations of dissolved and distributed hydrogen or monosaccharides present in the anaerobic reactor may inhibit operations of methane-forming microorganisms.

In another aspect, increased production of fuel values from organic substances can be accomplished by application of an electric field to cause dissociation of substances such as acetic acid (CH8COOH) that are produced by bacterial breakdown of glucose and other organic compounds and by other acid-production processes that yield hydrogen ions.

CH8COOH→CH8COO−+H+    Equation 4

Hydrogen ions migrate or are delivered to the negatively charged electrode and gain electrons to produce hydrogen gas.

2H++2e−→H2    Equation 5

Two electrons are supplied by the negatively charged electrode. At the other electrode the electrochemical reaction includes oxidation of the acetate ion to carbon dioxide and hydrogen ions as summarized in Equation 6.

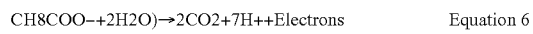

CH8COO−+2H2O)→2CO2+7H++Electrons    Equation 6

In this electrode reaction, acetate ions lose electrons, subsequently react with the water and break up into carbon dioxide gas and hydrogen ions. Carbon dioxide saturates the solution and is released from the liquid solution interface as set forth in the above embodiments. Hydrogen ions are circulated and/or migrate until electrons are received from the opposite electrode to produce hydrogen atoms and then diatomic molecules as summarized in Equation 5 for separate co-collection in such systems. Separated collection is highly advantageous, for example, separated collection to cause pressurization or at high pressure as a result of liquid pumping instead of gas compression, is especially efficient and greatly reduces the capital equipment ordinarily required to separate and then mechanically compress the hydrogen, methane or carbon dioxide produced.

Decomposition by anaerobic digestion of compounds such as acetic acid to produce hydrogen and carbon dioxide requires much less energy than electrolysis of water, because, in part, the digestion reactions yield hydrogen ions and exothermic energy. Initialization and maintenance of the exothermic decomposition of acids such as acetic acid may be accomplished at lower voltage applications or by intermittent or occasional electrolysis instead of continuous electrolysis as typically required to decompose water. The free energy of formation of water at ambient temperature is quite large (at least 1 KWH=3,412 BTU of released hydrogen) compared to the electrolysis of digester substances and acids such as urea and acetic acid to hydrogen and carbon dioxide, which requires relatively minimal activation and/or catalytic action particularly by organic catalysts. Accordingly, selected catalysts including modifications to Raney-Nickel catalysts, nickel-tin-aluminum alloys, selections from the platinum metal group, platinum-nickel and other platinum-transition metal single crystal alloy surfaces, and various organic catalysts utilized in conjunction with the electrode systems set forth herein further improve the rate and/or efficiency of hydrogen production.

In another aspect, it may be preferred to utilize numerous cells of electrode pairs connected in switchable series or parallel or series-parallel for purposes of matching the available source amperage and voltage with the voltage required for dissociation by series connection of cells such as shown in FIG. 1. In one aspect of this embodiment, each cell may require about 0.2 to 2 volts depending upon the aqueous electrolyte chosen or biochemically produced from organic substances so a home-size 6-volt photovoltaic source could have 3 to 30 cells in series and an industrial 220-volt service may have about 100 to 1,000 electrode cells connected in series. Product gases could readily be delivered by parallel or series collection arrangements. Depending upon the desired flexibility for adjusting the number of series and/or parallel connections, support and flow control feature 18 may be by an insulating or non-insulating material selection.

At various current densities, including at medium and low current densities, it may be preferred to allow buoyant propulsion of the bubbles that are generated to accomplish circulation of the electrolyte to prevent ion depletion and stagnation problems. At start-up or higher current densities one can operate pump 36 and heat exchanger 56 to provide the desired operating temperature and presentation of ion-rich electrolyte at the electrode surfaces. This enables extremely high rates of energy conversion in which energy such as off-peak electricity available from solar, wind, falling water, or wave resources is utilized to quickly and efficiently produce high-pressure supplies of oxygen and hydrogen or hydrogen and carbon dioxide or hydrogen and methane along with carbon dioxide for separated storage and use.

In one aspect of this embodiment, the problem of regenerative braking of vehicles or power-plant spin-down in which sudden bursts of large amounts of energy must be quickly converted into chemical fuel potential is addressed. A conventional fuel cell for truck, bus, or train propulsion cannot tolerate high current densities that are suddenly applied to the fuel cell electrodes. This embodiment overcomes this limitation and provides extremely rugged tolerance of high current conditions while achieving high electrolysis efficiency without the problems of PEM degradation or electrode-interface failures that regenerative PEM fuel cells suffer. Because of the rugged construction and extremely ample opportunities for cooling that are provided, extremely high current operations are readily accommodated. Conversely, this embodiment readily starts up and operates efficiently in severe cold or hot conditions without regard for various PEM-related difficulties, limitations, and failures.

In another aspect, in order to achieve much higher return on investment in energy conversion systems such as a hydroelectric generating station, wind farm, system of wave generators, or conventional power plants, the embodiment allows off-peak electricity to be quickly and efficiently converted into hydrogen and oxygen by dissociation of water or hydrogen and carbon dioxide by dissociation of substances generated by anaerobic digestion or degradation of organic matter. A compact version of the embodiment can occupy a space no larger than a washing machine and convert off-peak electricity that might otherwise go to waste into enough hydrogen to operate two family size vehicles and provide the energy requirements of the home.

As set forth above, some embodiments provided herein provide more efficient mass transport including rapid ion replenishment processes and deliveries to desired electrodes by pumping actions of low-density gases escaping from denser liquid medium. This assures greater electrical efficiency, more rapid dissociation, and greater separation efficiency along with prevention of undesirable side reactions. Increasing the rate and efficiency of ion production and delivery to electrodes increases the system efficiency and current limit per electrode area. Applications that convert organic substances into carbon dioxide and hydrogen or methane are particularly benefited by: enhanced rates of delivery of organic substances to microorganisms that participate in the process, incubation and delivery of incubated microorganisms to extend and self-repair biofilm media, more rapid separation of produced gases and delivery of organic substances along with more efficient delivery of intermediate ions to electrodes.

Referring to FIG. 4, another embodiment, electrolytic cell 100 is shown that is particularly beneficial in applications in which it is not desired to apply voltage or to pass current through the inside walls of containment vessel 102. The embodiment also facilitates series connections of bipolar or multiple electrode sets or cells such as 110 and 114 within the electrolytic cell 100 to simplify gas collection and voltage matching needs.

In one aspect in which that containment vessel 102 is cylindrical and the components within are concentric, electrode assemblies 110 and 114 may be formed from numerous nested truncated conical components or one or both electrodes may be formed as a helical electrode as described above. Electrodes 110 and 114 may be of the same, similar or different configurations. In another aspect, electrode 114 may be assembled from nested truncated conical sections or it may be a spiral electrode that continuously encircles electrode 110.

Figure 5:
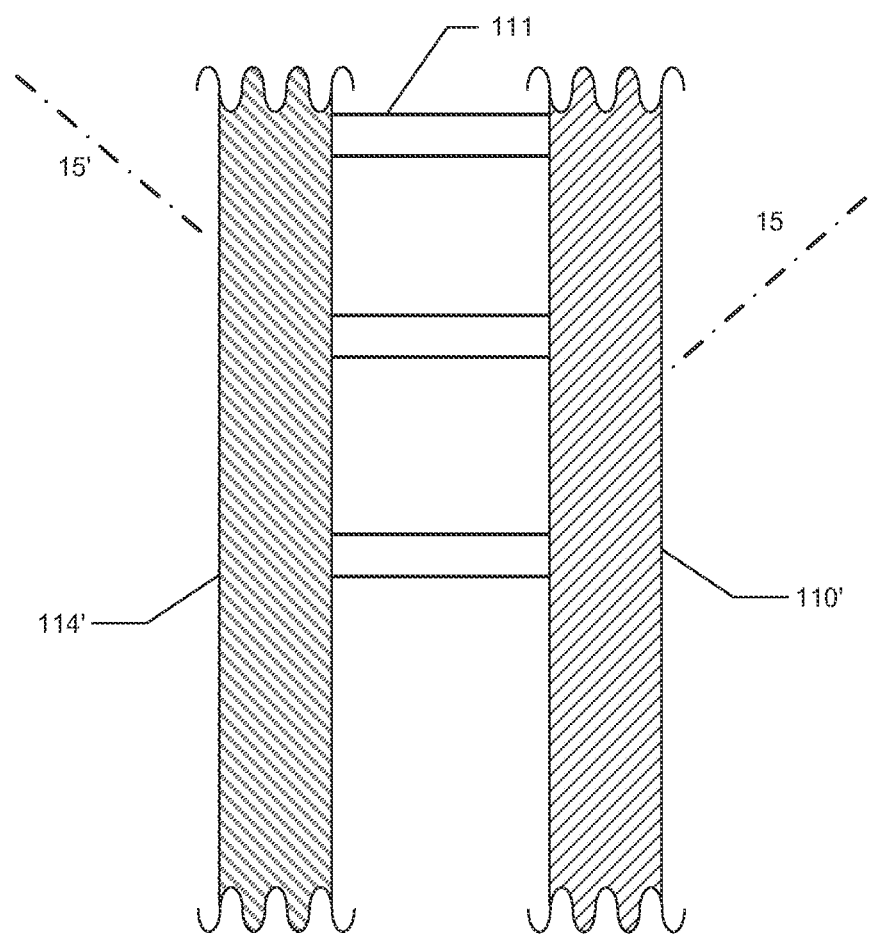
FIG. 5 a magnified view of an alternative embodiment for a portion of electrolytic cell of FIG. 4 in accordance with aspects of the disclosure.

Electrical separation of electrodes 110 and 114 to prevent short circuits may be accomplished by various means including by controlled tolerances for the operating dimensions and/or by the use of dielectric threads or filaments placed between electrodes 110 and 114 and/or by another form of separator 10 or 111 as disclosed regarding FIGS. 2 and 5.

The electrolytic cell 100 may be pressurized. Pressure containment is provided by upper and lower caps 104 and 106 as shown. Insulators 120 and 122 are supported by caps 104 and 106 as shown. The circuit components and hardware for electrical and fluid connections are illustrative and can be accomplished by penetrations through caps 104 and 106 as needed to meet specific application needs.

In the current embodiment, both electrodes 110 and 114 are formed to have inclined surfaces that direct the substance produced such as gas released to respective collection zones as shown. Illustratively, if water is to be dissociated from a suitable electrolyte, electrode 110 may receive electrons that are supplied through connection 108, which is sealed in cap 106 by plug seal 132. Electrons are thus taken from electrode 114 through plug seal 130, which provides insulation of contact 124 as a gas such as carbon dioxide or oxygen is released on electrode 114.

Such gases are thus propelled by buoyant forces and travel more or less upward as delivered by electrode 114 and along the inside wall of container 102. Hydrogen is propelled upward as delivered by electrode 110 and within the center core formed by numerous turns or conical layers of electrode 110 and collected as shown at insulator 120. Purified hydrogen at design pressure is delivered by pressure fitting 116. Catalytic filter 134 may be used to convert any oxidant such as oxygen that reaches the central core to form water. A similar catalytic filter material may be used to produce water from any hydrogen that reaches the outer collection annulus in insulator 120 as shown. Pressurized filtered oxygen is delivered by pressure fitting 118.

Optionally, to improve the efficiency of the electrolytic cell 100, one or more gas collection vessels (not shown) may be in fluid communication with electrolytic cell 100 to collect gas formed during electrolysis. The gas collection vessel can be implemented to capture the gas at an elevated pressure prior to substantial expansion of the gas. The gas collection vessel can be further configured to capture work as the gas expands according to methods known in the art. Alternatively, the gas collection vessel can be configured to provide gas at pressure for storage, transport or use wherein the gas is desired to be delivered at an elevated pressure. It is further contemplated that said aspect can be implemented in various electrochemical cells.

Referring to FIG. 2, in another aspect, a gas expander may be included at, near or inside fitting 22, fitting 26 or in a gas collection vessel in fluid communication with fitting 22 or fitting 26. Similarly, referring to FIG. 4, a gas expander may be included at, near or inside fitting 116, 118 or in a gas collection vessel in fluid communication with fitting 116 or fitting 118.

In another aspect, a method and apparatus for electrolysis to pressurize a fluid coupled with a device to extract work from such pressurized fluid is provided. The fluid may be pressurized liquid, liquid-absorbed gas, vapor or gas. Conversion of pressurized fluid to vapor or gas may occur in or after fitting 116 and a device to convert the pressure and flow from such fittings could be selected from a group including a turbine, generator, vane motor, or various piston motors or an engine that breathes air and injects pressurized hydrogen from 116. Similarly conversion of pressurized fluid to vapor or gas could be in or after fitting 118 and a device to convert the pressure and flow from such fittings could be selected from a group including a turbine, generator, vane motor, or various piston motors or an engine that expands and/or combusts pressurized fluid such as oxygen from 118.

In another aspect, an apparatus and method to overcome the high cost and power losses of a transformer and rectifier circuit is provided. This is accomplished by adjusted matching of load voltage with source voltage by series connection of electrode cells or electrodes within a cell, such as connecting the negative polarity of a DC source to the lowest three turns of electrode 110 to the next three turns of electrode 114 to the next three turns of electrode 110 to the next three turns of electrode 114 and to the next three turns of electrode 110 et seq. and starting from the opposite (highest) end to connect the positive lead from the DC source to three turns of electrode 114 to the next three turns of electrode 110 to the next three turns of electrode 114 to the next three turns of electrode 110 to the next three turns of electrode 114 et seq. Turns and/or stacks of truncated cones may be adjusted to develop the area needed to match the source amperage.

In another aspect of this embodiment, in addition to providing separation of the gases produced by electrolysis, the pumping action developed by the invention provides for delivery of nutrients to microorganisms that, depending upon the relative scale of operations, are hosted in suitable media such as carbon cloth, activated carbon granules, expanded silica, graphite felt, coal, charcoal, fruit pits, wood chips, shredded paper, saw dust, and/or mixtures of such selections that are generally located within portions of electrode 110 and/or between portions of electrode 114 and container 102. Corresponding functions and benefits include thermal stabilization of the system, circulation of feedstocks and removal of products such as carbon dioxide and production of hydrogen from acids that may be produced by the incubation, nutrition, and growth of such microorganisms.

At low and medium current densities, buoyant forces induced by low density solutions and bubbles can circulate the electrolyte within container 102. At higher current densities it is advantageous to adaptively control temperature, pressure, and circulation of the electrolyte as previously disclosed. External circulation of electrolyte may be from fitting 126 to fitting 138 as shown and includes situations in which one or numerous electrode cells connected in optional series and/or series-parallel circuits are contained within container 102.

In another aspect, the embodiment can be optimized for high current densities to deliver commensurately higher electrolyte fluid flow rates through one or more holes or grooves 139, which direct fluid at a tangent to the annular space between electrodes 110 and 114. Electrolyte flows upward along the helical spaces formed by the electrodes and is replenished by electrolyte entering helical paths provided by 110 and 114 from the annular space between 110 and 114. The angular momentum of the electrolyte entering the space between electrodes 110 and 114 increases the impetus of bubble lift pumping by electrolytic products such as hydrogen and oxygen respectively produced on electrodes 110 and 114 and adds to such momentum.

This circulation of electrolyte is highly beneficial for purposes of assuring rapid replacement of ions that become hydrogen and oxygen atoms or other gases such as carbon dioxide upon charge exchanges to and from electrodes 110 and 114 and for removing such gases for collection and removal with minimum electrical polarization loss during electrolysis. Thus very high current densities are readily accepted to efficiently electrolyze the circulated fluid. In another aspect, further accommodation of high current densities is provided by the vast cooling capacity of the design resulting from improved electrolyte circulation, which prevents harmful stagnation of products of electrolysis and/or phase changes such as steam nucleation, and reduction of effective electrode areas.

In another aspect, electrodes 110 and 114 may constitute spring forms that can be advantageously operated at a resonant frequency or perturbed by various inducements including piezoelectric drivers, rotating eccentrics, and the action of bubble formation and the acceleration thrust by less-dense mixtures of electrolyte and bubbles as higher density electrolyte inventories are delivered to the surfaces of electrodes 110 and 114 by the pumping action that results. In response to perturbation, electrodes 110 and 114 vibrate at natural or induced frequencies to further enhance dislodgement of bubbles from surfaces including nucleation sites and thus enable higher current densities and greater energy-conversion efficiency.

Induced vibration of helical spring-form electrodes such as 110 and 114 can also cause peristaltic mechanical action to enhance bubble acceleration toward the respective collection paths and exit ports of electrolytic cell 100. During this vibration, cyclic increases and decreases of the average distance and angle between adjacent layers of electrode turns produce fixed or traveling nodes depending upon the magnitude and frequency of the inducement(s).

FIG. 5 shows a representative section view of a set of electrodes 110' and 114' for operation in conjunction with an electrically insulative spacer 111 between 110' and 114' including selections such as insulator 10 shown in FIG. 2 that includes a helical flow delivery configuration for various applications or electrolytes. The assembly of concentric electrode 110', spacer 111, and electrode 114' provides a very rugged, self-reinforcing system for enabling efficient dissociation of fluids such as water, liquors from anaerobic digesters, or seawater with improved efficiency and resistance to fouling. Electrodes 110' and 114' may be constructed from conductive carbon papers, cloth, or felt; woven or felt carbon and metal filaments, graphite granules sandwiched between woven carbon or metal filaments; or metal-plated polymers or metallic sheet stocks such as mild steel, nickel plated steel, or stainless steel that are drilled more or less as previously disclosed with multitudes of holes on parallel centerlines that are inclined as shown for respective separations of hydrogen from co-produced gases such as oxygen, chlorine, or carbon dioxide depending upon the chemical make up of the electrolyte.

In instances that electrode 110', spacer 111, and electrode 114' are utilized in concentric electrode deployments such as shown in FIG. 4, hydrogen is delivered to port 116 and depending upon the substance undergoing dissociation, products such as oxygen, chlorine or carbon dioxide delivery is provided at port 118. In some instances it is preferred to provide the multitude of holes in 110' and 114' such that each hole is slightly tapered from the hole diameter on surface contacting spacer 111 to a larger diameter at the exit surface away from spacer 111.

It is preferred to select the helical pitch, width between electrodes, and thickness of the strip comprising spacer 111 for delivery of electrolyte from 138 to and through electrodes 110' and 114' to fitting 126 at rates that are commensurate with the electrical power available and the system heat transfer requirements to optimize the resulting width space between electrodes. This results in abundant deliveries of ions for electrolysis processes at electrodes 110' and 114' while assuring separation of hydrogen to the zone within electrode 110' and delivery of co-produced gases such as oxygen, carbon dioxide, or chlorine to the space outside of electrode 114'.

In another aspect, it is possible to operate the system regeneratively by providing gas flow grooves in the hydrogen electrode and gas flow grooves in the oxygen electrode along with appropriate fittings for adding hydrogen to the bottom of the hydrogen electrode and oxygen at the bottom of the oxygen electrode. In this case it may be advantageous to utilize concentric spiral electrodes particularly in small fuel cells where a single canister assembly meets energy needs.

Figure 6:
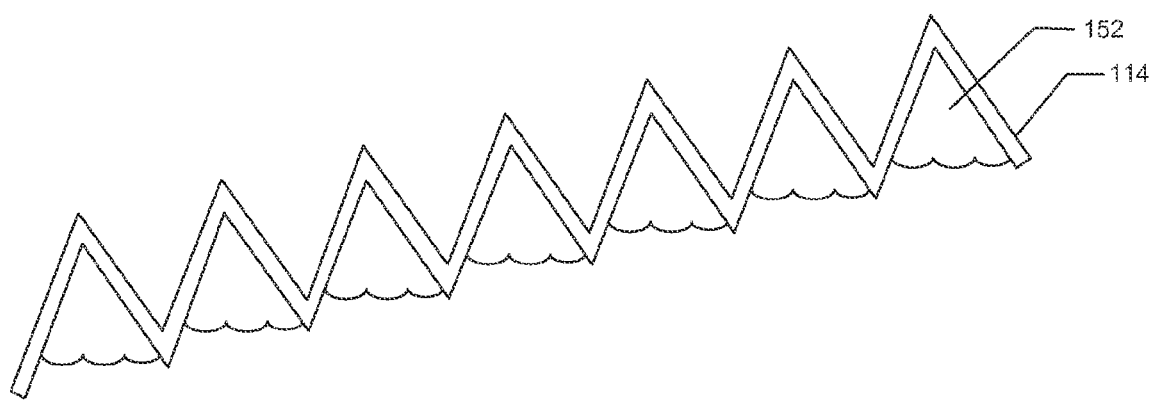
FIG. 6 shows a cross-section of a spiral electrode for use in a reversible fuel-cell in accordance with aspects of the disclosure.

Referring to FIG. 6, a cross-section of a spiral electrode(s) for use in instances that reversible fuel-cell operation is shown. This provides improvement of the surface to volume ratio, section modulus, and column stability of electrode 114 or of a similar helical version of electrode 110. Electrode 114 is illustrated in the section with gas 152 flowing along spiral grooves formed by corrugating the strip stock that is used to form the spiral and provide delivery of oxygen for fuel-cell operation and in electrolysis operation to deliver oxygen to annulus 136 and fitting 118. The same configuration works well for electrode 110 in fuel-cell and electrolysis modes for conversion of organic acids into carbon dioxide and hydrogen and in the electrolysis mode and assures plentiful gas delivery to the desired collection or source ports as previously described.

In another aspect, improved electrode performance is provided by facilitating the growth and maintenance of microorganisms that convert aqueous derivatives of organic substances such as carbonic, acetic, butyric and lactic acids along with compounds such as urea into hydrogen. On the electrode chosen for production of hydrogen ions and/or the release of carbon dioxide, increased microbe productivity is facilitated by preparing such electrode surfaces with topographical enhancements that increase the effective surface area including high aspect ratio filaments or whiskers that reduce electrical resistance to the substrate electrode and help hold microbes and biofilm in place along with the desired film substances provided by digestive processes.

Without being limited by theory, it is believed that the specific features of the electrode and/or separator, such as the topographical treatments or enhancement, promote turbulence, including cavitation or super cavitation, of the electrolyte at a desired location which in turn promotes nucleation at the location. Conversely, the specific configuration of the electrode and/or separator can inhibit turbulence, including cavitation or super cavitation at a desired location, for example, the point of electron transfer, which in turn inhibits nucleation at that location. It is contemplated that elements including these features can be implemented at any location in the electrolytic cell at which nucleation is desired. Moreover these same features and principles can be applied to a gas collection vessel or similar in fluid communication with the electrolytic cell, or to fluid communication with passages or valves there between.

Suitable filaments and or whiskers include metals or doped semiconductors such as carbon, silicon or nano-diameter filaments of carbon or boron nitride to provide increased surface area, reduce ion-transport and ohmic loses, increased microbe productivity and more effective nucleation activation for more efficient carbon dioxide release. Such filaments may also be utilized to anchor graphite granules that further improve microbe productivity, enhanced efficiency of enzyme and catalyst utilization, and related beneficial hydrogen ion production processes. Similarly, at the electrode where hydrogen ions are provided with electrons to produce hydrogen atoms and nucleate bubbles of diatomic hydrogen, filaments and whiskers may be utilized to increase the active area and reduce the voltage required for the overall process.

In addition to carbon whiskers, filaments grown from metals such as tin, zinc, nickel, and refractory metals deposited from vapor or grown from plating on suitable substrates such as iron alloy electrodes, have been found to provide reduced electrical resistance and improved process efficiency. Such filaments or whiskers may be made more suitable for biofilm support and process enhancement by addition of conducive surfactants and or surface plating with suitable substances such as carbon, boron nitride, or silicon carbide deposited by sputtering or from decomposition of a substance such as a carbon donor from illustrative precursors such as acetylene, benzene, or paraffinic gases including methane, ethane, propane, and butane.

The embodiment of FIG. 4 and variation thereof can provide advantageous separation of low density gaseous derivatives of fluid dissociation including hydrogen separation from organic liquors as summarized in Equations 1-6 to deliver hydrogen or selections of hydrogen-enriched mixtures to port 116 while carbon dioxide or carbon dioxide enriched mixtures including fixed nitrogen components are delivered to port 118. In some applications it may be desirable to reverse the polarity of these electrodes to reverse the delivery ports for gases that are separated. Such reversals may be long term or intermittent to accomplish various purposes. Depending upon selections of helical pitch(es) of electrodes 110 and 114 and each electrode's resonant or imposed frequency of vibration, and the relative fluid velocity at each electrode, hydrogen may be delivered to port 116 but the system may be operated to include methane and carbon dioxide. However, carbon dioxide delivered to port 118 may include methane and other gases of greater density than hydrogen. In applications that it is desired to provide Hy-Boost mixtures of hydrogen and methane to enable unthrottled operation of internal combustion engines, various burners, furnaces or fuel cells, the embodiment of FIG. 4 operating with hydraulic and electrical circuit control provisions such as provided by pump 36 and controller 52, facilitates the option of producing and separating desired fuel mixtures with controlled ratios of hydrogen and methane for delivery at port 116.

An unexpected but particularly beneficial arrangement for production of vigorous anaerobic colonies of microbes that produce the desired conversion of organic feedstocks to hydrogen and/or methane is provided by adding media such as colloidal carbon, carbon filaments including nanostructures, exfoliated carbon crystals, graphene platelets, activated carbon, zeolites, ceramics and or boron nitride granules to the electrochemical cell. Such media may be doped or compounded with various agents to provide enhanced catalytic productivity. Illustratively, desirable functionality may be provided by doping with selected agents having electron structures more or less like boron, nitrogen, manganese, sulfur, arsenic, selenium, silicon, tellurium, and or phosphorous. Circulation induced by the gases released by the electrolysis process can promote sorting of such media into advantageous locations and densities for more efficient charge current utilization.

Without being limited to a particular theory, it is hypothesized that such synergistic results relate to increased surface areas in critical locations and development of stringers, regions, or filaments that enhance nucleation processes and or conduct electrons or hydrogen ions along with advantageous adsorption of enzymes, hydrogen, methane or carbon dioxide in biofilms and reaction zones that result. It is also indicated that microbes are incubated for circulation to efficiently utilized locations in the operations performed and flow paths produced in various embodiments disclosed herein.

In addition to whiskers and filaments such as carbon, graphite, various metal carbides, and silicon carbide and other inorganic substances and particles that catalytically enhance performance, it is beneficial to utilize activated substances and particles that present desired nutrients or catalysts to assist microbial processes. Illustratively, porous and/or exfoliated substrates of polymers, ceramics or activated carbon may adsorb conductive organic catalysts such as co-tetramethoxyphenylporphirine (CoTMPP) or poly(3,4-ethylenedioxythiophene) (PEDOT) and or favorably orient and present other catalytic substances including enzymes and graft polymers that may also be utilized to incorporate and present catalytic substances including additional enzymes.

Suitable substances or graft polymers may include those of conventional, dendrimers, fiberforms, and other organic functional materials to minimize or replace platinum and other expensive catalysts and conductors. Such replacement substances and their utilization include mixtures or staged locations with respect to the fluid circulation resulting from some embodiments disclosed herein. Variously specialized conductive and or catalytic structures include acicular deposits and fibers that may be grown or attached to the electrodes 4, 8, 110, or 114 and/or to overlaid carbon felts or woven structures or dispersed into developing biofilms. Illustratively, conductive and/or catalytic functionalities may be provided by filaments that retain and present hydrogenase and other enzymes, CoTMPP and or other catalysts such as poly (3,4-ethylenedioxythiophene) (PEDOT) as fibers that are synthesized from aqueous surfactant solutions as self-organized thin-diameter, nanofibers with an aspect ratio of more than 100 and provide low resistance to charge conductivity. Synthesis in aqueous solutions including anionic surfactant sodium dodecyl sulfate (SDS) can be adapted to produce various configurations by changing the concentrations of SDS and furthermore by adding FeCl3 to produce polymerized structures. (An exemplary procedure is described in Moon Gyu Han et al., Facile Synthesis of Poly (3,4-ethylenedioxythiophene) (PEDOT) Nanofibers from an Aqueous Surfactant Solution, Small 2, No. 10, 1164-69 (2006), incorporated herein by reference.) Other examples include functional catalysts and micro-conductors in the form of nanocomposites derived from cellulose nanofibers and semiconducting conjugated polymers including polyaniline (PANI) and a poly (p-phenylene ethynylene) (PPE) derivative with quaternary ammonium side chains. Cellulose, carbon, or ceramic whiskers with anionic surface charges can be combined with positively charged conjugated polymers to form stable dispersions that can be solution cast from polar solvents such as formic acid.

Preparations include graft polymers and end caps of organometallic alkoxides, metal alkyls and application of the catalytic benefits of acetic acid and a polymeric catalyst containing COOH end group. Special function and bifunctional end groups along with mixtures of end groups may be chosen to produce multi-functional characteristics including catalytic functions, reactive stabilizers, grafting agents, and promoters of dispersion polymerization. Similarly, specialized activation of carbon or other substrates by hydrogen and or enzymes produced by anaerobic microorganisms provides a locally hydrogen-rich environment to enhance or depress methane production and enhance additional hydrogen production from various organic substances.

Referring to FIGS. 1-3, optionally it may be advantageous to provide one or more supplemental felts and or woven screens of carbon filaments to the outside and inside surfaces of cylindrical components 8, 10, 11, 110, and or 114. Such supplemental felts and or woven screens may commensurately collect or distribute electrons in conjunction with electrodes 4, 8, 110, and or 114 and or separators 10 or 11 and help anchor or preferentially locate granules, filaments, and or other structures to reduce pressure losses or more equally distribute liquor flows and facilitate microbial functions in the desired energy conversion operations.

Among the complementary and competing reactions and processes to provide net production of hydrogen and carbon dioxide are various steps of processes summarized in Equation 8.

$$Carbon + 2H_2O \rightarrow CO_2 + 4H^+ + 4\ Electrons \qquad \text{Equation 8}$$

carbon is consumed as summarized in Equation 8 including carbon that may be supplied as a constituent or a carbonaceous substance mixed with liquor from an anaerobic digester or electrolyzer or as a result of various manufacturing outcomes. Illustratively, carbon may include scrap from grinding, machining, electro-discharge-machining (EDM), and various thermochemical operations to produce electrodes, electrode coatings on electrodes including tank liners, or particles, or filaments, or flocculants, or selected carbides by thermal dissociation and reaction processes, including colloidal or other suspensions as an outcome of various degrees of dehydrogenization of organic substances.

Such carbon and/or carbon-donor feedstocks may be renewably supplied by bacteria, phytoplankton, or larger algae that receive carbon dioxide and other nutrients from the liquor supplied or by circulation of carbon dioxide to hydroponic and or soil-supported plants. It is advantageous to utilize such forms of carbon with high surface to volume ratios and to provide a voltage gradient to zones where they are delivered for the purpose of driving the reaction indicated and for delivering hydrogen ions to electrode surfaces including complementary conductive media such as filaments and conductive filter substances for production, nucleation, and release of hydrogen bubbles to increase the overall rate of hydrogen production.

Suitable provisions for increasing active surfaces and or flocculants include those with organic constituents such as bacteria, proteins, simple and complex sugars, cellulose, thermally dissociated cellulose, live and dissociated phytoplankton along with various forms of colloidal carbons, activated carbons, and carbides. Illustratively, phytoplankton and or larger algae may be grown, dried, mixed with a binder such as corn syrup, thermally dehydrogenated to various extents and milled to provide finely divided flocculants. Alternatively, activated carbon feedstocks may be milled to provide finely divided particles that are utilized as enzyme receivers or flocculent media or it may be used in conjunction with the previously disclosed substances to enhance the desired production or efficiency of enzymes, to support incubation of desired microorganisms, or to increase hydrogen or methane production and or consumption of carbon to produce hydrogen ions for electrolysis as indicated by Equation 8.

If needed, occasional use of salt water or additions of small amounts of salt to water-based electrolytes can produce chlorine to quickly disinfect or to prevent harmful fouling of the electrolyzer systems shown. Utilization of some embodiments, for example FIG. 5, enables the resulting system to be inherently free of harmful fouling even when utilizing electrolytes such as wastewater, commercial process water, wood-ash water, sea water, fly-ash water, canal and ditch water, or anaerobic digester liquor. Further, such systems can be quickly cleaned if needed by backflow of electrolyte or cleaning water from fitting 118 to 138 to dislodge particles that may have been delivered to the electrodes.

Applications of some embodiments include large community waste disposal operations to nano-size electrolyzers, include improvements to conventional waste digesters from which solutions or "liquor" containing organic substances is supplied for production of hydrogen and/or methane and or carbon dioxide and other plant nutrients. In this capacity some embodiments can provide rapid and efficient conversion of byproducts produced by anaerobic digesters and convert hydrogen ions into hydrogen and overcome acid degradation of the methane production operations. In operation, liquor from an anaerobic digester is utilized to produce hydrogen and carbon dioxide to provide beneficial restoration and or maintenance of pH near 7.0 instead of more acidic conditions that may stymie methane production systems. This enables increased overall energy conversion efficiency as it overcomes the requirement for expensive provisions for addition of chemical agents to adjust the pH in digesters. In such medium and large applications it is beneficial to design and engineer multifunctional components including electron distribution circuits that may also provide desired retention of granules such as carbon, boron nitride, zeolites, polymers, and ceramics including such substances in variously activated conditions for enhanced performance.

In another aspect, an electrolyzer such as disclosed herein may be applied to provide rapid conversion of acids that are typically produced by anaerobic digestion including applications with municipal waste water and landfills along with wastes form slaughter houses, dairies, egg farms, and other animal feeding centers or similar. Production of methane is slowed or inhibited if acids that are produced by anaerobic conditions cause the pH to fall much below 7. Such acids can form if the feed rate of organic material exceeds the capacity of the methanogenic colony of microorganisms. By extracting hydrogen from such acids the rate of organic material processing by anaerobic digestion can be increased. The combination of methane and hydrogen provides much greater net energy production per ton of wastes, and the wastes are processed faster to increase the capacity of the process.

A particularly useful embodiment of the some embodiments is in waste-to-energy applications that utilize organic substances such as sewage along with hydrolyzed garbage, farm wastes, and forest slash in the anaerobic electro-digestion process summarized in Equations 1-6 to produce hydrogen with minimal or no oxygen production. The rugged configuration and recirculation operations enable great tolerance for dissolved solids including organic solids and particles in anaerobic process liquors that are utilized as electrolytes. Production of hydrogen without commensurate release of oxygen as would be released by electrolysis of water facilitates higher efficiency and safety for utilization of the waste-sourced hydrogen as a cooling gas in electrical equipment such as an electricity generator.

Figure 7:
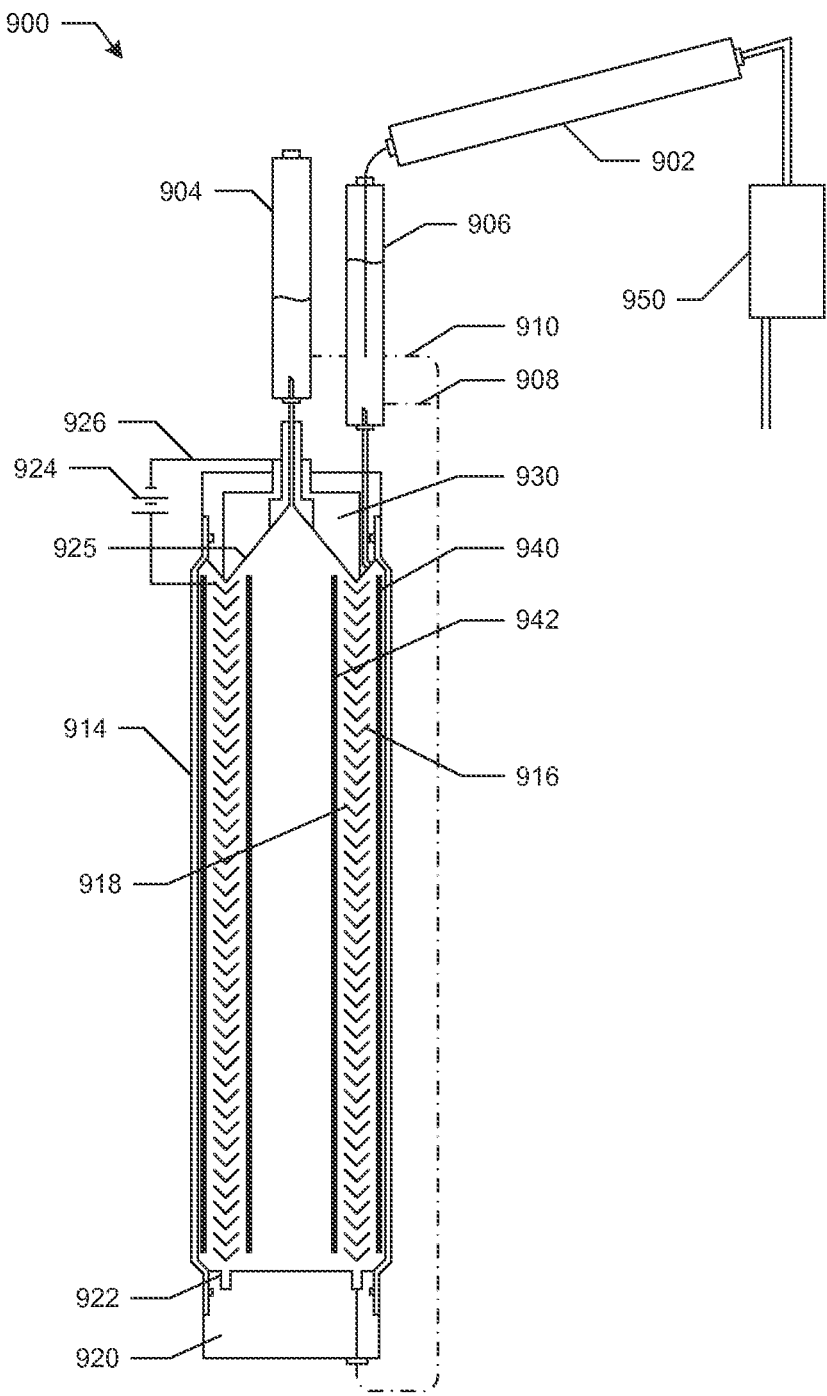
FIG. 7 shows a system for converting organic feedstocks such as those produced by photosynthesis into methane, hydrogen, and or carbon dioxide in accordance with aspects of the disclosure.

In another application of some embodiments disclosed herein, electrolyzer system 900 as shown in FIG. 7 provides for tissue and/or cellular disruption of biomass by enzyme, mechanical, thermal, acoustic, electrical, pressure and/or chemical actions and processes in conditioner 950 to enable faster or more complete processing, digestion and/or support of incubator purposes. Fluid including such disrupted cells from conditioner 950 and related feedstocks that are produced by converter 902 is circulated to electrolyzer 914 through annular distributor 922 of base 910 as shown. Anaerobic microorganisms are supported by media 940 and 942 and receive liquid recirculated from hydrogen separator 904 through conduit 910 and liquid recirculated from carbon dioxide separator 906 through conduit 908 as shown. Electrode 918 and/or media 942 releases hydrogen and electrode 916 and/or media 940 releases carbon dioxide. Electromotive bias is provided to electrodes 916 and 918 through circuit 926 by source 924 which may range from 0.1 to about 3 VDC depending upon the compound dissociation requirement and occasional needs for increased voltage to overcome insulating films that form. Hydrogen is ducted to collection and delivery to separator 904 by travel along the more or less conical surface 925, which may be a conductive surface depending upon the desired series/parallel variations or contained and supported by insulator 930 as shown.

In operation, liquors are mingled in distributor annulus 922 and travel upwards to provide process reactants and nutrients to microorganisms hosted in activated carbon cloth and/or granules 940 and 942 and or conductive felts that encase and substantially retain such granules proximate to electrode 916 and or 918. Smaller particles and filaments may be added to infiltrate locations throughout the electrolyzer system to enhance electrical charge conductivity, enzyme, and catalytic functions including those previously disclosed. Separator 902 may be a reverse osmosis membrane or a cation or anion exchange membrane or it may be constructed according to the embodiments shown in FIG. 2, 3, 4, or 5 and in some instances such separators may be used in conjunction with each other as may be desired to provide for various liquor circulation pathways and/or to produce hydrogen and carbon dioxide at different pressures or with a pressure differential between hydrogen and carbon dioxide.

Similarly, numerous circulation options are available if electrode 916 along with adjacent felt and or media 940 operates as electron sources to produce hydrogen from ions delivered from liquors that are circulated by the action of gas production lifts, convection currents, or by pump deliveries as shown. In this option, carbon dioxide is released as hydrogen ions are produced from acids delivered from 902 and 950 or that are produced by microorganisms hosted in fibrous or granular media 942 and associated felt materials that are electrically biased by electrode 918 to be opposite to electrode 916 as shown. Another exemplary option results if electrons are supplied by electrode 918 to produce hydrogen that is collected by insulator 930 for delivery to gas collector 904 as shown. In this instance electrode 916 and the media electrically associated with it are electron collectors as carbon dioxide is released to provide pumping in the fluid circuit shown as carbon dioxide is delivered past insulator 930 to collector 906 as shown.

Referring to FIG. 7, system 900 can be used for converting organic feedstocks such as those produced by photosynthesis into methane, hydrogen, and/or carbon dioxide and/or by microorganisms. Depending upon the microorganisms that are hosted, liquors that typically include acids such as acetic and butyric acids along with compounds such as urea are dissociated in electrolyzer 914. Electrolyzer 914 provides current at sufficient voltage to produce hydrogen from such compounds and acids and may provide operation as a digester and an electrolyzer, or may be operated within an anaerobic digester (not shown) or may utilize liquors produced by anaerobic digestion in 914 as shown. Such operation is particularly useful for converting organic wastes from a community and or industrial park for purposes of supplying the community with fuel and feed stocks for manufacturing carbon enhanced durable goods.

2. Architectural Crystal

As described above with reference to FIGS. 1-7, the electrolytic cell 2 is configured to electrolyze and electrolyte. According to certain embodiments of the disclosure, the electrolytic cell 2 can be at least partially made from an architectural construct as disclosed in U.S. patent application Ser. No. 13/027,214, now U.S. Pat. No. 8,980,416, entitled "ARCHITECTURAL CONSTRUCT HAVING FOR EXAMPLE A PLURALITY OF ARCHITECTURAL CRYSTALS," filed on Feb. 14, 2011. For example, the architectural construct can be composed of a synthetic matrix characterization of crystals that can be specifically designed to achieve desired (1) thermal properties, (2) electromagnetic, optical, and acoustical properties, (3) catalytic properties, (4) capillary properties, and (5) sorptive properties. The architectural construct can be designed to utilize some or all of these properties for a particular application, such as facilitating hydrogen production. The architectural construct's behavior depends on its composition, surface structures located on its layers, it layer orientation, its dopants, and the coatings (including catalysts) that are applied to its surfaces. When it is configured as layers, its behavior also depends on the thicknesses of its layers, spacers between its layers, the distances separating its layers, and the means used for supporting its layers and/or separating its layers. An architectural construct is a macro-structure designed to facilitate micro-processing on a nano-scale. From a macroscopic standpoint, it can be configured to have a specific density, modulus of elasticity, and/or section modulus. And it can be designed so that from a microscopic standpoint it acts as a molecular processor, charge processor, and/or bio processor.

Figure 8A:
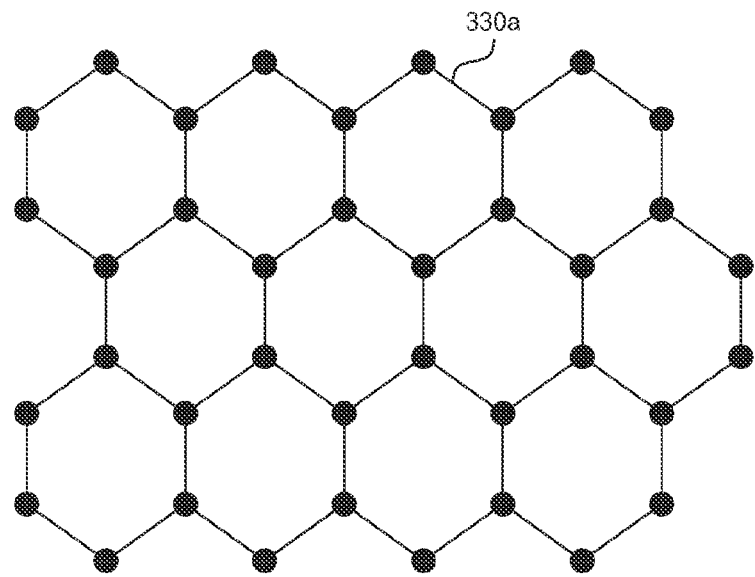
FIGS. 8A and 8B are molecular diagrams of architectural constructs of the disclosure.

The electrolytic cell 2 or the separator 10 or the electrolyte can include an architectural construct for facilitating hydrogen production and can be configured in many ways. For example, a designer can arrange it as a solid mass (e.g., as multiple single-atom-thick layers stacked upon each other), as multiple spaced apart layers that are individually as thin as an atom, or in another configuration through which it will exhibit a desirable property. A designer can also dope the architectural construct or coat its surfaces with a substance, each of which causes it to behave in a different way than it would have otherwise. Illustratively, FIG. 8A is a molecular diagram of a layer of a matrix characterization of crystals 330*a* of an architectural construct. The layer 330*a* may include carbon, boron nitride, or another suitable substance. For example, the matrix characterization of crystals may be a layer of graphene. A layer of a matrix characterization of crystals can be configured as an architectural construct by specializing the layer, such as by doping the layer or arranging the layer with other layers in a particular configuration so that the resulting construct exhibits a particular property. Layers 330*a* of a matrix characterization of crystals that form an architectural construct can be configured stacked together as a layer that is thicker than an atom (e.g., graphene stacked to form graphite) and/or spaced apart from each other by particular distances. Furthermore, layers of an architectural construct can be oriented with respect to each other in various ways.

Figure 8B:
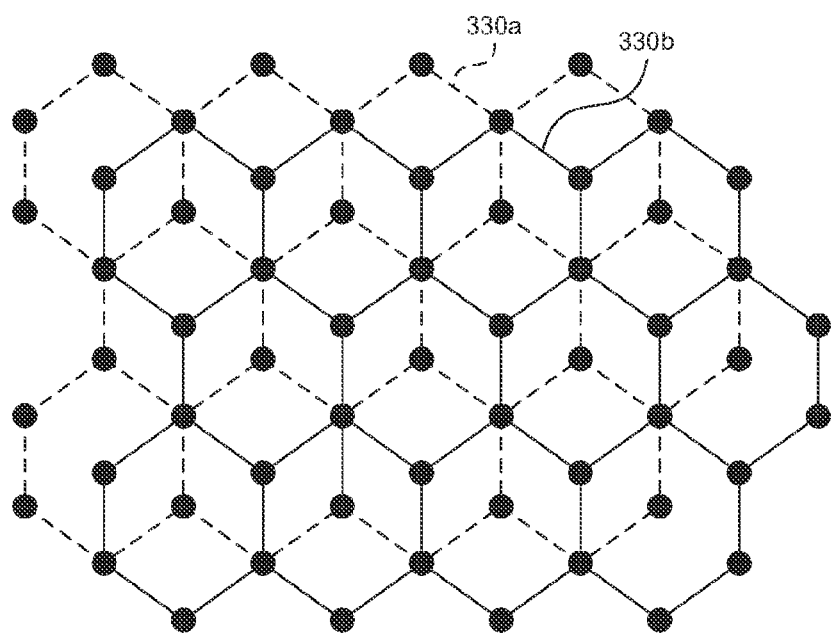

FIG. 8B is a schematic molecular diagram of an architectural construct including a second layer 330*b* of a matrix characterization of crystals stacked on the first layer 330*a* of a matrix characterization of crystals of FIG. 8A (the first layer 330*a* is shown in broken lines in FIG. 8B). Referring to FIGS. 8A and 8B together, the layers consists of graphene, which is an atom-thick planar sheet of carbon. In some implementations, a single atom-thick sheet of a matrix characterization of crystals is made of another substance besides carbon, like boron nitride. In still further embodiments, the architectural construct may be configured as a solid mass. A solid mass architectural construct can consist of, for example, graphite or boron nitride. An architectural construct configured as a solid mass includes multiple single-atom-thick layers stacked together. An architectural construct configured as a solid mass is specialized, meaning it has been altered to behave in a specific way or to perform a predetermined function. In some implementations, a solid mass is specialized by doping or by orienting its single-atom thick layers a particular way with respect to one another.

In some implementations, first and second layers of an architectural construct are configured so that atoms of the first layer and atoms of the second layer vertically aligned when viewed from above. For example, the molecules of an architectural construct consisting of two layers that are aligned in this manner will appear like the first layer 330*a* of the architectural construct from FIG. 8A when viewed from above. In other embodiments a first layer can be rotated relative to a second layer by 30-degrees. In some implementations, a first layer of an architectural construct includes a first substance, such as carbon, and a second layer of the construct includes a second substance, such as boron nitride. Layers composed of or doped with different substances may not appear planar as larger molecules warp the planar surface. As further detailed below, some properties of an architectural construct are influenced by the orientation of its layers relative to each other. For example, a designer can rotate or shift a first layer of a construct relative to a second layer of the construct so that the construct exhibits particular optical properties, including a specific optical grating Moreover, the layers of the architectural construct can be oriented in a position with respect to each other (i.e., offset and/or rotated as discussed above with respect to FIGS. 8A-8B) by applying trace crystal modifiers, such as neon, argon, or helium, at the time of a layer's deposition, through a heat treat that moves the molecules to a particular orientation, or through torque of the crystal during exfoliation.

An architectural construct configured in accordance with embodiments of the disclosure can be composed of a single substance (e.g., graphene, boron nitride, etc.) or it can be specialized by being doped or reacted with other substances. For example, an architectural construct consisting of graphene may have areas that are reacted with boron to form both stoichiometric and non-stoichiometric subsets. The graphene can be further specialized with nitrogen and can consist of both graphene and boron nitride graphene with a nitrogen interface. In some implementations, compounds are built upon the architectural construct. For example, from a boron nitride interface, a designer can build magnesium-aluminum-boron compounds. By specializing an architectural construct in these ways, a designer can create a construct that exhibits different properties than a construct composed of only one substance would.

Figure 8C:
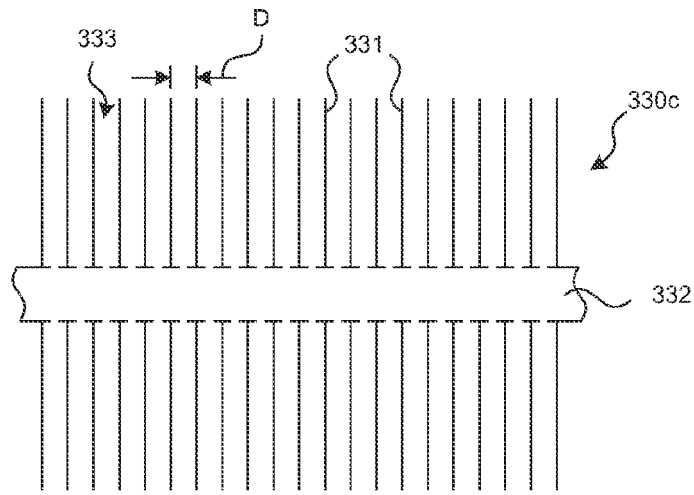
FIGS. 8C-8D and 8F are cross-sectional side views and FIG. 8E is an isometric cross-sectional view of corresponding architectural constructs configured with parallel and spaced apart layers in accordance with aspects of the disclosure.

Architectural constructs including parallel layers spaced apart from one another are capable of yielding a wide range of properties and achieving many outcomes. For example, FIG. 8C is a cross-sectional side view of an architectural construct 330c configured as parallel and spaced apart layers 331 that can be comprised of any of a number of substances, such as graphene, graphite, or boron nitride. The parallel layers 331 may be rectangular, circular, or other suitable shapes. In FIG. 8C, the layers 331 include an opening or hole through which a support tube 332 supports the architectural construct 330c. The layers 331 are each separated by a distance D creating zones 333 between the layers 331. The individual layers 331 of the architectural construct 330c can be made to have any suitable thickness. In FIG. 8C, for example, each of the parallel layers 331 can be a single atom thick. For example, each layer may be a sheet of graphene. In some implementations, the layers of the architectural construct are thicker than one atom. In still other embodiments, the layers 331 can have different thicknesses, as well as be spaced apart by different distances.

Figure 8D:
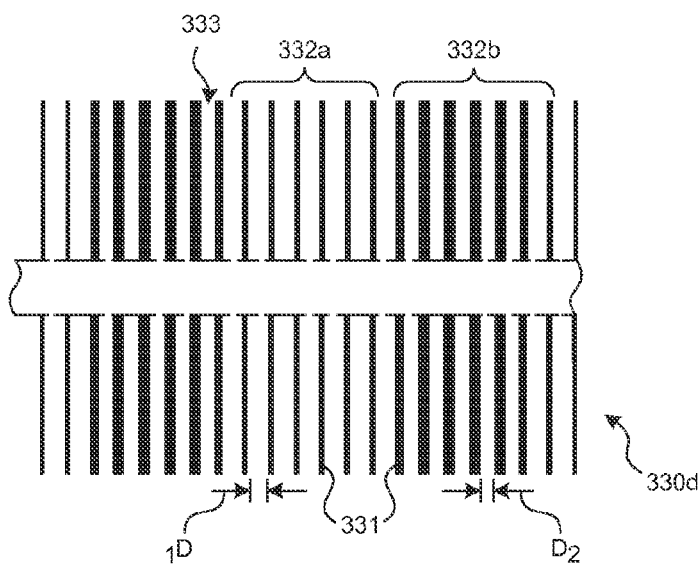
Figure 8E:
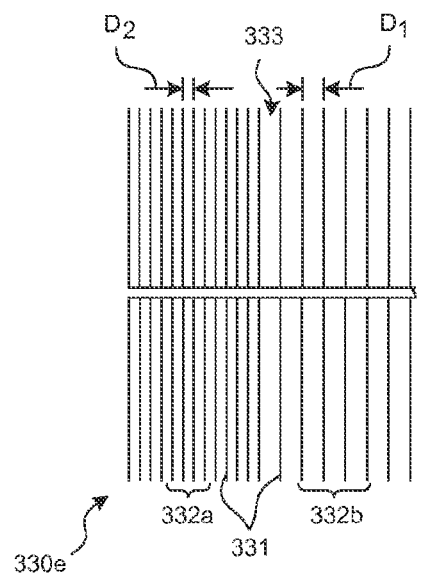

FIG. 8D, for example, is a cross-sectional side view of an architectural construct 330d with multiple layers 331 of different thicknesses or widths. In certain embodiments, the layers 331 are each thicker than one atom. In other embodiments, however, some of the layers 331 may be only a few atoms thick and other layers 331 may be much thicker, such as 20 atoms or more. More specifically, the layers 331 can include a first group 332a of relatively thin layers 331, and a second group 332b of relatively thicker layers 331. According to additional features of the illustrated embodiment, the first group 332a of layers 331 can include a first distance $D_1$ between adjacent layers 331 that is greater than a second distance $D_2$ between adjacent layers 331 of the second group 332b. These spacing distances accordingly create zones 333 between adjacent layers 331. FIG. 8E is a cross-sectional side view of an architectural construct 330e with multiple layers 331 having approximately the same thickness but that are spaced apart from one another by varying distances. For example, a first group 332a of layers 331 can be spaced apart from each other by a first distance D1 that is less than a second distance D2 spacing apart corresponding layers 331 of a second group 332b. FIG. 8E also illustrates the zones 333 between the adjacent layers 331. The zones 333 are sized according to the spacing distances between the layers 331, therefore creating, for example, larger zones 333 in the second group 332b than in the first group 332a.

Figure 8F:
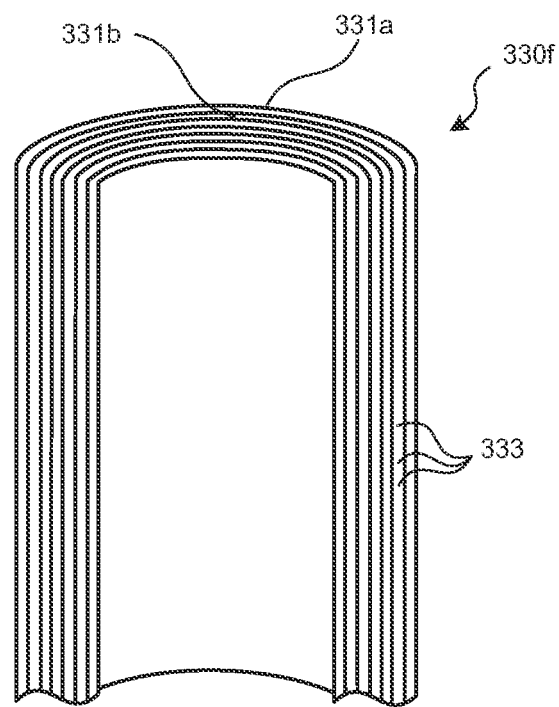

FIG. 8F is a cross-sectional isometric partial view of an architectural construct 330f consisting of concentric tubular layers 331 of a matrix characterization of crystals. For example, a first layer 331a of the architectural construct 330f is tubular and has a greater diameter than an adjacent second layer 331b. The architectural construct 350f can include multiple concentric layers spaced apart in this manner.

Figure 8G:
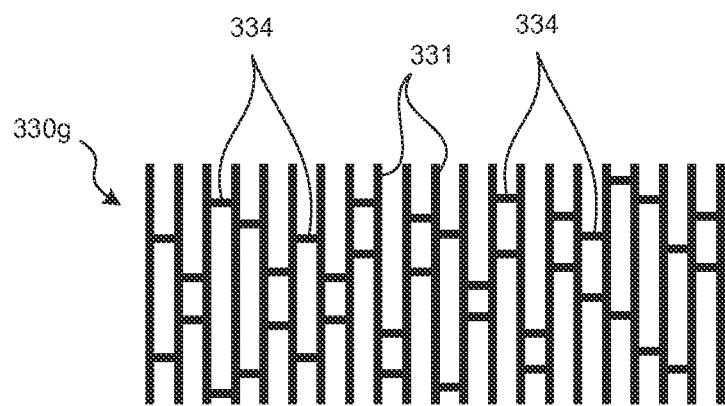

Turning next to FIG. 8G, FIG. 8G is a side cross-sectional partial side view of an architectural construct 330g illustrating several spacers 334 between adjacent layers 331. In certain embodiments, the spacers can be composed of titanium (e.g., to form titanium carbide with a graphene layer), iron (e.g., to form iron carbide with a graphene layer), boron, nitrogen, etc. To form the configuration shown in FIG. 8G, in some implementations a gas is dehydrogenated on the surface of each layer 331, thereby creating the spacers 334 where each molecule is dehydrogenated. For example, after a layer 331 of the architectural construct 330g is exfoliated, methane may be heated on the surface of the layer 331, which causes the methane molecules to split and deposit carbon atoms on the surface of the layer 331. The larger the molecule that is dehydrogenated, the larger the spacing or spacer 334 that is created. For example, propane, which has three carbon atoms per molecule, will create a larger spacer 334 than methane, which has one carbon atom per molecule. In some implementations, the spacers 334 are surface structures, like nanotubes and nanoscrolls, which transfer heat and facilitate in the loading of substances into the architectural construct the 330g. Architectural constructs that include these types of surface structures are described U.S. patent application Ser. No. 12/857,515, filed on Aug. 16, 2010 and entitled "APPARATUSES AND METHODS FOR STORING AND/OR FILTERING A SUBSTANCE" which is incorporated herein by reference in its entirety.

An architectural construct including any of the configurations described above can be formed in a variety of ways, as described in detail in U.S. patent application Ser. No. 13/027, 214, now U.S. Pat. No. 8,980,416, entitled "ARCHITECTURAL CONSTRUCT HAVING FOR EXAMPLE A PLURALITY OF ARCHITECTURAL CRYSTALS," filed on Feb. 14, 2011, as well as in U.S. Pat. No. 6,503,584 and pending U.S. patent application Ser. No. 12/857,515, now U.S. Pat. No. 8,147,599, each of which is incorporated herein by reference in its entirety. These methods can include, for example, forming layers or an architectural construct by dehydrogenating a gas (e.g., a hydrocarbon) within a frame to form the first layer, and to dehydrogenate a substance (e.g., titanium hydride) to form spacers on the inside surface of the layer before dehydrogenating the gas to form the second layer on the spacers or surface structures. Subsequent layers can then be deposited in a similar fashion. Other methods can include machining a single crystal into a desired shape and exfoliating the single crystal into layers. Further approaches can include diffusing a fluid (e.g., hydrogen) into a crystal and exfoliating layers from the crystal. These layers can be exfoliated a predetermined distance away from an adjacent layer. Moreover, spacers or surface structures can also be deposited between the layers.

Several features of the architectural constructs as disclosed herein and in U.S. patent application Ser. No. 13/027,214, now U.S. Pat. No. 8,980,416, entitled "ARCHITECTURAL CONSTRUCT HAVING FOR EXAMPLE A PLURALITY OF ARCHITECTURAL CRYSTALS," filed on Feb. 14, 2011 and incorporated by reference herein in its entirety, can be specifically designed to produce hydrogen and/or electrolyze an electrolyte of the electrolytic cell 2 as described above with reference to FIG. 1. For example, an architectural construct can be designed so that it has a specific density, modulus of elasticity, and section modulus. These macroscopic characteristics affect the properties that an architectural construct exhibits at the microscopic level. More specifically, an architectural construct's density is defined as its mass per unit volume, which can be affected by a number of different parameters. One parameter is the composition of the matrix characterization of crystal. For example, a crystal of boron nitride generally has a higher density than a crystal of graphite. Another parameter is the distance separating the layers of an architectural construct. Increasing or decreasing the spacing between the layers will correspondingly increase or reduce an architectural construct's density. An architectural construct's density will also be greater in embodiments in which its layers are spaced apart by spacers relative to embodiments in which the layers are similarly spaced but not by spacers. Dopants that are added to an architectural construct will also affect the density (e.g., the greater the amount of dopants, the greater the corresponding density).

Another property of an architectural construct that can be specifically designed is the modulus of elasticity, which is its tendency to be deformed elastically when a force is applied to it (e.g., defined as the slope of its stress-strain curve in the elastic deformation region). Like its density, an architectural construct's modulus of elasticity depends in part on the thicknesses of its layers, their spacing, and their composition. Its modulus of elasticity will also depend on how the layers are fixed relative to one another. For example, if the layers are supported by a central tube or support, the individual layers can generally elastically deform by a greater amount than if they are fixed relative to one another using spacers. When spacers fix two layers relative to one another, each layer will reinforce the other corresponding layer when pressure is exerted on either layer, thereby dampening the deflection that results from a given force. The amount that each layer reinforces each other is contingent, in part, on the concentration of spacers between the layers and how rigidly the spacers hold the layers together.

An additional property of an architectural construct that can be specifically designed is the section modulus, which is the strength of the architectural construct or ratio of a cross section's second moment of area to the distance of the extreme compressive fiber from the neutral axis. An architectural construct's section modulus will depend on the size and shape of each layer of architectural construct. An architectural construct's density, modulus of elasticity, and section modulus, as well as other macroscopic properties, can be constant throughout the architectural construct or they can vary by section or cyclically. Just as an architectural construct's density, modulus of elasticity, or section modulus can affect the properties that are exhibited by the architectural construct, varying these macroscopic characteristics either by section or cyclically can cause the architectural construct to behave differently at different parts or sections of the construct. For example, by separating an architectural construct's layers in a first section by a greater amount than in a second section (thereby giving it a greater density in the second section than in the first), the architectural construct can be made to preferentially load, collect, or otherwise accumulate a first substance in the first section and a second substance in the second section.

Figure 9:
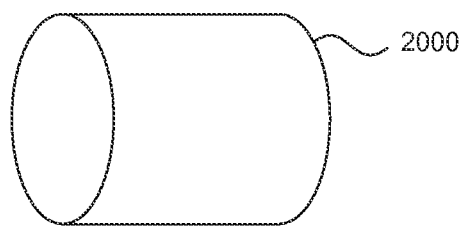
FIG. 9 is an isometric view of an architectural construct configured as a solid mass.

FIG. 9 shows an isometric view of an architectural construct 2000 that is configured as a solid mass. The architectural construct 2000 can include, for example, graphite or boron nitride. An architectural construct configured as a solid mass includes multiple single-atom-thick layers stacked together in various orientations. An architectural construct configured as a solid mass is specialized, meaning it has been altered to behave in a specific way. In some implementations, a solid mass is specialized by doping or by orienting its single-atom-thick layers a particular way with respect to one another.

An architectural construct can be composed of a single substance (e.g., boron nitride) or it can be specialized by being doped or reacted with other substances. For example, an architectural construct including graphene may have areas that are reacted with boron to form both stoichiometric and non-stoichiometric subsets. The graphene can be further specialized with nitrogen and can include both carbon graphene and boron nitride graphene with a nitrogen interface. In some implementations, compounds are built upon the architectural construct. For example, from a boron nitride interface, a designer can build magnesium-aluminum-boron compounds. In some implementations, the edges of a layer of an architectural construct are reacted with a substance. For example, silicon may be bonded on the edges to form silicon carbide, which forms stronger bonds between the construct and other matter and changes the construct's specific heat. By specializing an architectural construct in these ways, a designer can create a construct that exhibits different properties than a construct composed of only one substance.

Figure 10:
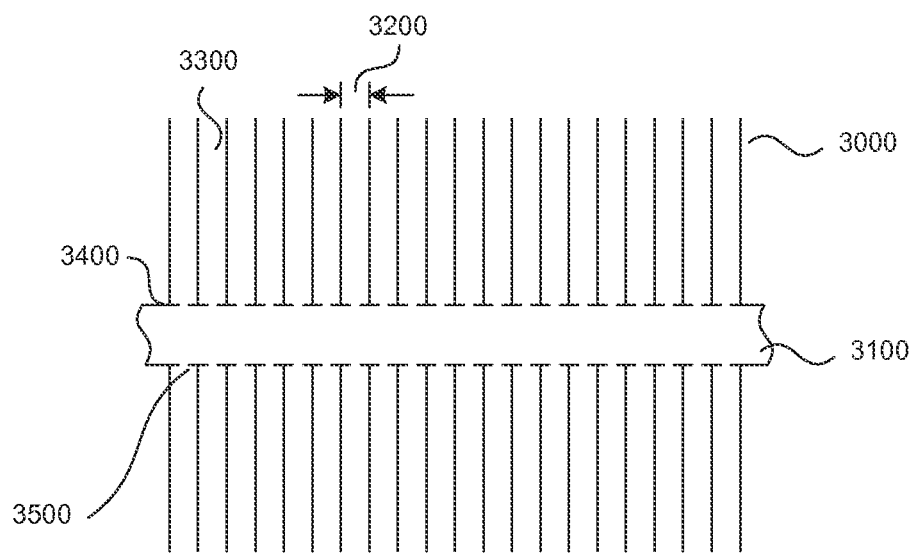
FIG. 10 is a cross-sectional side view of an architectural construct configured as parallel layers.

Architectural constructs including parallel layers spaced apart from one another are capable of yielding a wide range of properties and achieving many outcomes. FIGS. 10-18 show architectural constructs configured according to some implementations. FIG. 10 is a cross-sectional side view of an architectural construct 3000 configured as parallel layers. Parallel layers of an architectural construct may be comprised of any of a number of substances, such as graphene, graphite, or boron nitride. Parallel layers may be rectangular, circular, or another shape. In FIG. 10, the layers are circular and include a hole through which a support tube 3100 supports the architectural construct 3000. The layers are each separated by a distance 3200, characterizing zones 3300 between the layers.

Figure 11:
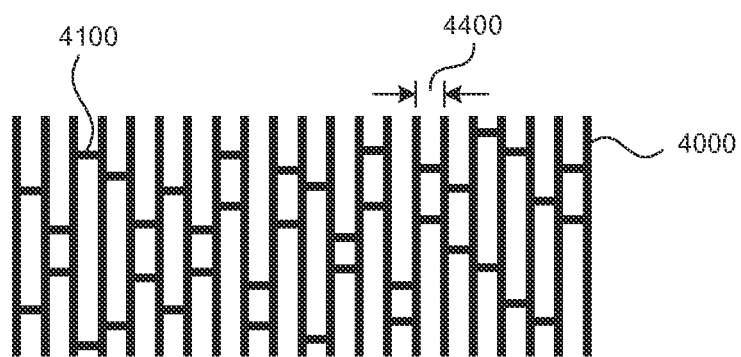
FIG. 11 is a side view of an architectural construct configured as parallel layers.

FIG. 11 is a side view of an architectural construct 4000 configured as parallel layers. The layers of the architectural construct 4000 are each thicker than one atom. For example, each layer may include multiple sheets of graphene stacked upon each other. An architectural construct may include parallel layers that are only a few atoms thick or layers that are much thicker, such as 20 atoms or more.

Figure 12:
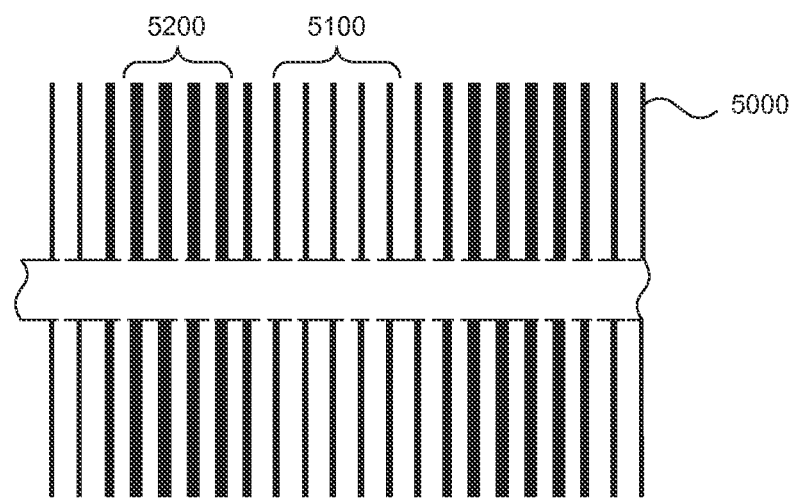
FIG. 12 is a cross-sectional side view of an architectural construct configured as parallel layers.

In some implementations, all the layers are the same thickness, while in other implementations the layers' thicknesses vary. FIG. 12 is a cross-sectional side view of an architectural construct 5000 configured as parallel layers that have various thicknesses. As discussed above, layers thicker than an atom or differing from one another in thicknesses may be exfoliated from a single crystal by controlling the depth to which a fluid is diffused into the crystal to exfoliate the layers (e.g., by introducing impurities or dopants at the desired depth).

When an architectural construct is configured as parallel layers, the layers may be spaced an equal distance apart or by varying distances. Referring again to FIG. 10, a distance 3200 separates each of the parallel layers characterizing zones 3300 between each layer that are approximately equal in size. In FIG. 12, the distances between the layers of the architectural construct 5000 vary. For example, the distance between the layers of a first set 5100 of layers is greater than the distance between the layers of a second set 5200 of layers, meaning that the zones between layers of the first set 5100 are larger than those of the second set 5200.

There are a number of techniques for arranging one layer a particular distance away from another layer. As mentioned above, one method is to configure the parallel layers on a support structure and exfoliate each layer a certain distance away from an adjacent layer. For example, a manufacturer can control both the volume of liquid and the distance that it is diffused into a single crystal for exfoliating a layer. Another method is to electrically charge or inductively magnetize each exfoliated layer and electrically or magnetically force the layers apart from one another. An adherent can secure the layers in place on the central tube at particular distances away from one another.

Another technique for establishing a particular distance between the layers is to deposit spacers between the layers. Spacers can be composed of titanium (e.g., to form titanium carbide with a graphene layer), iron (e.g., to form iron carbide with a graphene layer), boron, nitrogen, etc. Referring again to FIG. 11, the parallel layers 4000 are separated with spacers 4100. In some implementations, a gas is dehydrogenated on the surface of each layer, creating the spacers 4100 where each particle or molecule is dehydrogenated. For example, after a layer of an architectural construct is exfoliated, methane may be heated on the surface of the layer, causing the methane molecules to split and deposit carbon atoms on the surface of the layer. The larger the molecule that is dehydrogenated, the larger the spacing. For example, propane, which has three carbon atoms per molecule, will create a larger deposit and area or space than methane, which has one carbon atom per molecule. In some implementations, parallel layers are configured on a central tube and the spacers are included between the layers. In some implementations, the spacers are surface structures, like nanotubes and nanoscrolls, which transfer heat and facilitate in the loading of substances into an architectural construct. Architectural constructs that include these types of surface structures are described below with respect to FIGS. 17 and 18.

Figure 13:
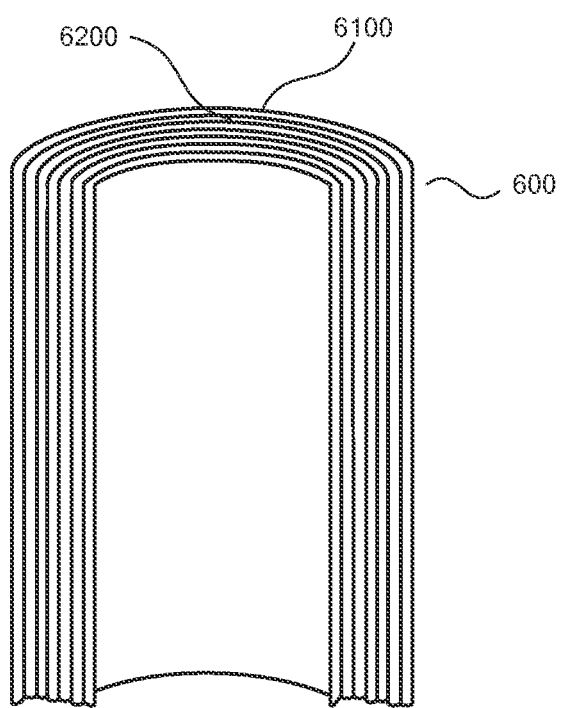
FIG. 13 is a cross-sectional side view of an architectural construct configured as concentric tubular layers.

FIG. 13 shows a cross-sectional side view of an architectural construct 600 configured as concentric tubular layers of a matrix characterization of crystals. For example, a first layer 6100 of the architectural construct is tubular and has a diameter greater than a second layer 6200 of the architectural construct, and the second layer 6200 is configured within the first layer 6100. An architectural construct configured as concentric tubes can be formed in many ways. One method is to dehydrogenate a gas, such as a hydrocarbon, within a frame to form the first layer 6100 of the architectural construct 6000, and to dehydrogenate a substance, such as titanium hydride, to form spacers on the inside surface of the first layer before dehydrogenating the first gas to form the second layer 6200 on the spacers. Subsequent layers can then be deposited in a similar fashion. In some implementations, each tubular layer is formed by dehydrogenating a gas in its own frame. The dehydrogenated layers are then configured within one another in the configuration shown in FIG. 13. Spacers can be deposited on either the inside or outside surfaces of the layers to space them apart by a particular distance. In other instances, multiple wraps of a material such as polyvinyl fluoride or chloride are dehydrogenated to produce the desired architectural construct. In other instances, polyvinylidene chloride or fluoride are dehydrogenated to produce the desired architectural construct.

Figure 14:
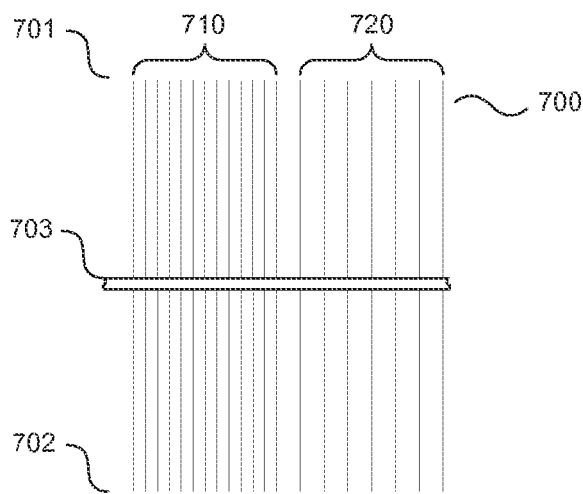
FIG. 14 is a cross-sectional side view of an architectural construct configured as parallel layers.
Figure 15:
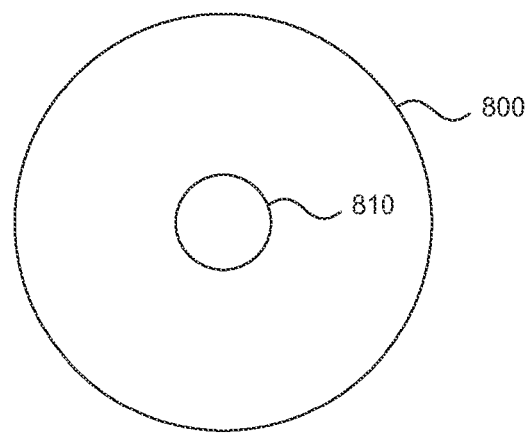
FIG. 15 is a side view of a layer of an architectural construct.
Figure 16:
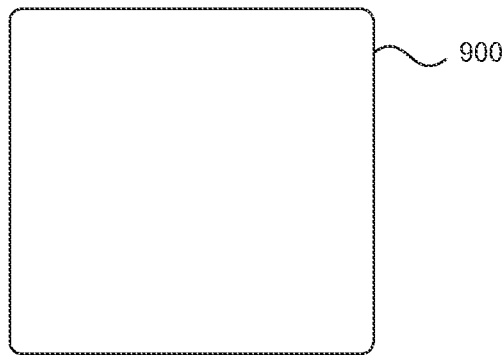
FIG. 16 is another side view of a layer of an architectural construct.

FIG. 14 is a cross-sectional side view of an architectural construct 7000 comprised of parallel layers. A first set 7100 of layers are spaced apart by a closer distance than a second set 7200 of layers. The architectural construct 7000 is discussed in further detail below with reference to some of the properties that it exhibits in this configuration. FIG. 15 is a side view of a layer 8000 of an architectural construct. The layer 8000 has a circular shape, and it includes a hole 8100, through which a support structure may support the layer 8000. FIG. 16 is a side view of a layer 9000 of an architectural construct that has a rectangular shape with rounded corners. As mentioned above, if a layer is exfoliated from a single crystal, it can be machined into a particular shape either before or after exfoliation. Multiple layers like the layer 9000 can be arranged together via, for example, a support structure configured on its edges or spacers configured on their surfaces.

In some implementations, an architectural construct is configured to be non-sacrificial. For example, as explained below, an architectural construct can be configured to load molecules of a substance into zones between layers of the construct. A non-sacrificial construct can load and unload substances or perform other tasks without sacrificing any of its structure. In other implementations, an architectural construct is configured to sacrifice atoms from its crystalline structure to facilitate a particular result. For example, an architectural construct that is composed of boron nitride may be configured to load nitrogen, which the boron nitride will facilitate reaction with hydrogen to form ammonia and/or other nitrogenous substances. As a result, atoms from the construct will be sacrificed in the reaction with hydrogen, and when the product is unloaded from the construct, the architectural construct will have lost the sacrificed molecules of boron nitride. In some implementations, a construct that has sacrificed its structure can be restored or cyclically utilized in such reactions. For example, an architectural construct that is composed of boron nitride can be restored by presenting the construct with new nitrogen, boron, or boron nitride molecules and applying heat or another form of energy such as electromagnetic radiation. The new boron nitride molecules may self-organize into the original shape of the architectural construct.

An architectural construct can be configured to catalyze a reaction in a variety of ways. For example, an architectural construct comprised of parallel layers, like those of FIGS. 10-12, may catalyze a chemical reaction or a biological reaction at an edge of its layers by controlling the temperature of the reaction, by having a particular configuration that catalyzes the reaction, or by supplying a substance that catalyzes the reaction. An architectural construct can catalyze a reaction by speeding the reaction up, prolonging the presentation of reactants to promote a reaction, enabling the reaction by heat addition or removal, or by otherwise facilitating the reaction.

A number of variables can be changed to catalyze a particular reaction. In some implementations, the thicknesses of the layers of an architectural construct are selected so that a reaction is catalyzed. In some implementations, the distances between layers and/or the layers' compositions (e.g., boron nitride, carbon, etc.) are selected so that a reaction is catalyzed. In some implementations, dopants are added to an architectural construct or spacers (including surface structures) of a particular chemistry are added between layers so that a particular reaction is catalyzed.

In some implementations, the parallel layers catalyze a reaction by transferring heat to a zone where a reaction is to occur. In other implementations, the parallel layers catalyze a reaction by transferring heat away from a zone where a reaction is to occur. For example, referring again to FIG. 10, heat may be conductively transferred into the parallel layers 3000 to supply heat to an endothermic reaction within the support tube 3100. In some implementations, the parallel layers catalyze a reaction by removing a product of the reaction from the zone where the reaction is to occur. For example, referring again to FIG. 10, the parallel layers 3000 may absorb alcohol from a biochemical reaction within the support tube 3100 in which alcohol is a byproduct, expelling the alcohol on outer edges of the parallel layers, and prolonging the life of a microbe involved in the biochemical reaction.

In some implementations, a first set of parallel layers is configured to catalyze a reaction and a second set of parallel layers is configured to absorb and/or adsorb a product of the reaction. For example, referring again to FIG. 12, the second set 5200 of layers may be configured to catalyze a chemical reaction by enabling the reaction between two molecules and the first set 5100 of layers may be configured to adsorb a product of the reaction, thus prolonging the length of the chemical reaction.

A reaction can be catalyzed in other ways as well. In some implementations, an architectural construct is electrically charged to catalyze a reaction proximate the construct. In some implementations, an architectural construct is configured to resonate acoustically at a particular frequency, causing molecules to orient themselves in a way that catalyzes a reaction. For example, the molecules may be oriented to enable a chemical reaction or their adsorption onto the layers. In some implementations, an architectural construct is configured to transmit or absorb radiant energy to catalyze a reaction. For example, referring to FIG. 12, the second set 5200 of layers may be configured to absorb radiant energy and transform the radiant energy into heat that the first set 5100 of layers uses to facilitate an endothermic reaction. Similarly, surface structures may be configured to absorb radiant energy to heat the construct and facilitate a reaction.

In some implementations, a catalyst is added to an architectural construct to catalyze a reaction proximate to the construct. The catalyst may be applied on the edges of layers of the construct or on the surfaces of the construct. For example, chromia may be applied on the edges of an architectural construct, and the chromia may catalyze a chemical reaction between methane and ozone produced from air using ionized ultraviolet radiation or an induced spark.

An architectural construct that is arranged in parallel layers may be configured to load a substance into zones between the layers. A molecule of a substance is loaded between parallel layers when it is adsorbed onto the surface of a layer or absorbed into the zones between the layers. For example, referring back to FIG. 10, the architectural construct 3000 may load molecules of a substance presented at an inside edge 3400 of the layers into the zones 3300 between the layers. The support tube 3100 may supply the substance through perforations 3500.

A number of factors affect whether an architectural construct will load molecules of a substance. In some implementations, the architectural construct is configured to transfer heat away from the zones where a molecule is loaded from. When an architectural construct is cooled, it may load molecules faster or it may load molecules that it was unable to load when it was hotter. Similarly, an architectural construct may be unloaded by transferring heat to the construct. In some implementations, an architectural construct is configured to load molecules at a faster rate or at a higher density when an electric charge is applied to the construct. For example, graphene, graphite, and boron nitride are electrically conductive. An architectural construct composed of these materials may be configured to load molecules at a higher rate when an electric charge is applied to its layers. Additionally, as mentioned above, in some implementations, an architectural construct can be configured to acoustically resonate at a particular resonant frequency. An architectural construct may be configured to resonate at a specific frequency so that particular molecules proximate to the construct are oriented favorably so that they can be loaded into the zones between the layers.

In some implementations, an architectural construct is configured to load or unload a substance when radiant energy is directed at the construct. For example, referring to FIG. 10, the distance 3200 between each of the parallel layers 3000 may be selected so that the architectural construct absorbs infrared waves, causing the layers to heat up and unload molecules of a substance that it has loaded. As discussed above, in some implementations, a catalyst can be applied to the outside edges of the layers to facilitate the loading of substances into the zones between the layers.

In some implementations, an architectural construct is configured to selectively load a particular molecule or molecules (e.g., by loading a first molecule and refraining from loading a second molecule). For example, referring again to FIG. 12, the first set 5100 of layers may be configured so that they are a particular distance apart that facilitates the selective loading of a first molecule and not a second molecule. Similarly, the second set 5200 of layers may be configured so that they are a particular distance apart to facilitate the loading of a third molecule but not the second molecule. Surface tension at edges of the layers will also affect whether a molecule is loaded into an architectural construct. For example, if the first set 5100 of layers has already loaded molecules of a first substance, surface tension at the inside edges of the first set 5100 of layers where molecules of the substance are loaded from may prevent the first set 5100 of layers from loading molecules of the second substance but allow the first set 5100 of layers to continue to load molecules of the first substance.

Figure 17:
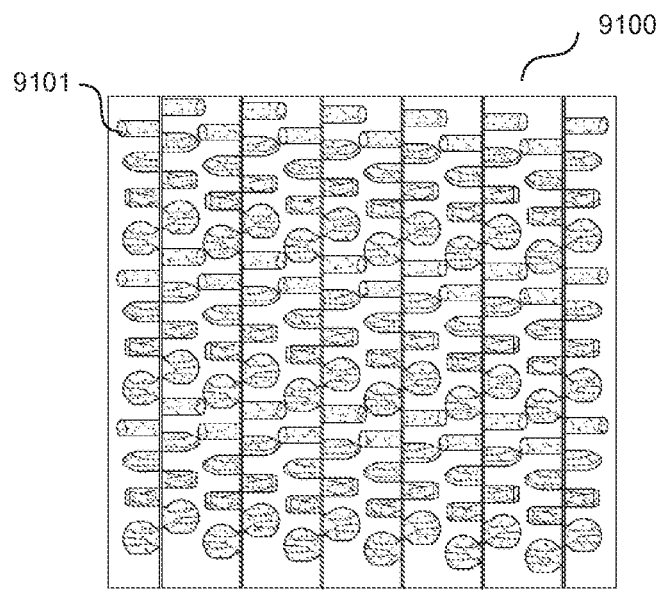
FIG. 17 is a side view of an architectural construct configured as parallel layers.

In some implementations, an architectural construct includes surface structures configured on its surfaces that facilitate in the loading and unloading of substances into and out of the construct. Surface structures can be epitaxially oriented by the lattice structure of a layer to which they are applied. In some embodiments, they are formed by dehydrogenating a gas on the surface of the layers. In other embodiments, they are coated on a layer before adjacent layers are configured on the construct. FIG. 17 shows an architectural construct 9100 that includes parallel layers that have surface structures 9101 configured thereon. The surface structures 9101 include nano-tubes, nano-scrolls, rods, and other structures.

Surface structures can enable an architectural construct to load more of a substance or load a substance at a faster rate. For example, a nano-flower structure can absorb molecules of a substance into an area within the structure and adsorb molecules of the substance on its surface. In some embodiments, the surface structures enable the architectural construct to load a particular compound of a substance. In some embodiments, the surface structures enable the architectural construct to load and/or unload molecules of a substance more rapidly. In some embodiments, a particular type of surface structure is preferred over another surface structure. For example, in some embodiments, a nano-scroll may be preferred over a nano-tube. The nano-scroll may be able to load and unload molecules of a substance more quickly than a nano-tube can because the nano-scroll can load and unload multiple molecules of a substance at the same time while a nano-tube can only load or unload one molecule at a time. In some embodiments, a first type of surface structure loads a first compound and a second type of surface structure loads a second compound. In some embodiments, surface structures are composed of material that is electrically conductive and/ or has a high availability for thermal transfer. In some embodiments, the surface structures are composed of carbon.

Figure 18:
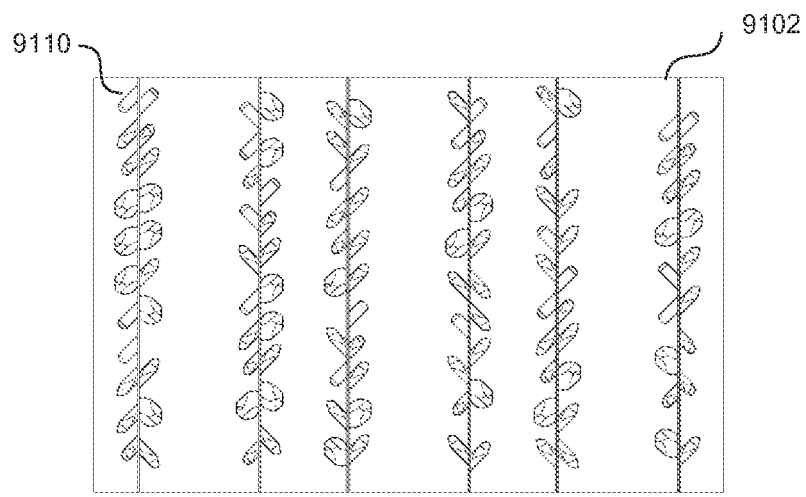
FIG. 18 is another side view of an architectural construct configured as parallel layers.

As is shown in FIG. 17, in some embodiments, surface structures are oriented perpendicular to the surfaces of the architectural construct. In other embodiments, at least some of the surface structures are not oriented perpendicular to the surface that they are applied on. In FIG. 18, surface structures

9110 are oriented at different angles from the surfaces of an architectural construct 9102 than 90-degrees. A surface structure may be oriented at a particular angle to increase the surface area of the surface structure, to increase the rate that molecules are loaded by the surface structure, to increase a loading density of the surface structure, to preferentially load a molecule of a particular compound, or for another reason. Surface structures can be configured, including inclination at a particular angle, by grinding, lapping, laser planning, and various other shaping techniques.

In some implementations, surface structures are configured on an architectural construct and are composed of a different material than the construct. In FIG. 17, for example, the layers of the architectural construct 9100 may be composed of graphene and the surface structures 9101 may be composed of boron nitride. The surface structures can be composed of other materials, such as boron hydride, diborane (B$_2$H$_6$), sodium aluminum hydride, MgH$_2$, LiH, titanium hydride, and/or another metal hydride or another compound.

3. Architectural Construct Enabled Hydrogen Production by Microbial Electrolysis, Fermentation, and/or Photosynthesis Biological hydrogen production offers the possibility of generating hydrogen that is renewable and carbon neutral as further described in Hyung-Sool Lee, Wim F. J. Vermass, and Bruce E. Rittmann, *Biological hydrogen production: prospects and challenges*, TRENDS IN BIOTECHNOLOGY, 28 at 262 (2010), herein incorporated in its entirety by reference. Efficient biological hydrogen production can be achieved in accordance with the teachings disclosed herein.

In accordance with aspects of the disclosure, inorganic electrolysis and biological hydrogen production applications in which microorganisms utilize H+ ions or protons as an electron sink for two electron exchanges provide processes that are summarized in Equation 1:

$$2H+ + 2e- \rightarrow H2 \quad \text{Equation 1}$$

Hydrogen produced by such processes including essentially similar electron sink steps in microbial electrolysis, fermentation and/or photosynthesis and can be separated as a gas that escapes from water because of its relatively low solubility. However all three variations of hydrogen production have losses that are attributable to competitive processes that consume hydrogen and prevent collection of the hydrogen. Thus, although the indicated electrons are provided, the amount of hydrogen provided for collection and subsequent applications is diminished because hydrogen is consumed by various competitive biological operations.

Figure 19A:
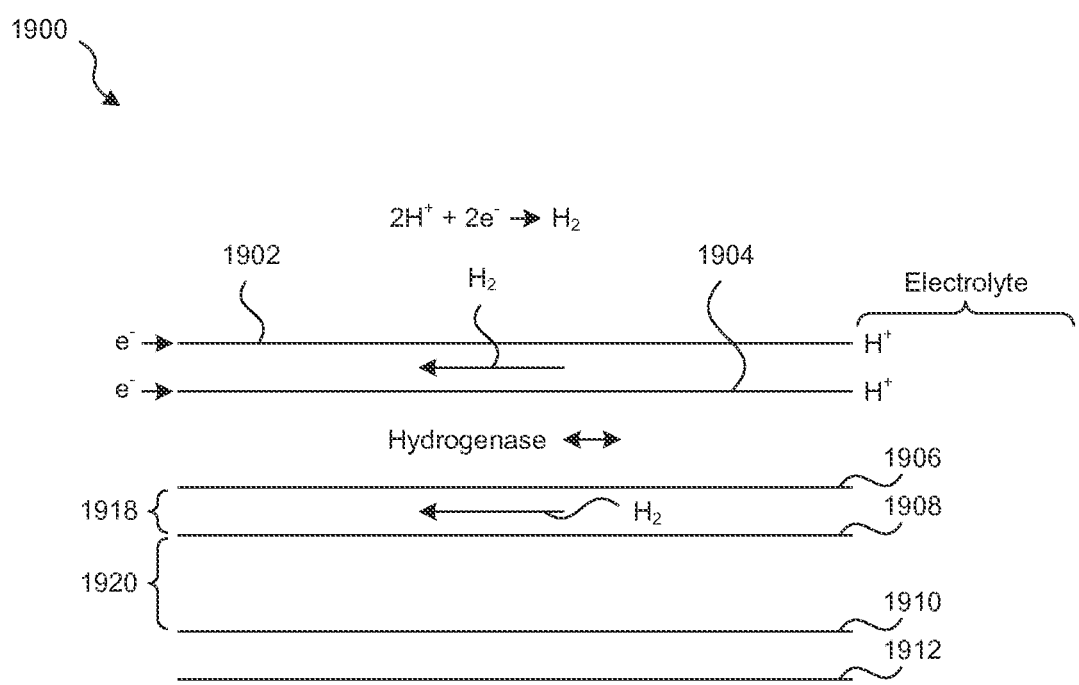
FIGS. 19A-19C are cross-sectional views of an electrode in accordance with aspects of the disclosure.

As shown further with respect to FIG. 19A, electrodes constructed from an architectural construct provide an isolation of hydrogen that is produced by removal between graphene layers which may also serve as superior electron conductors and provide catalytic functions along with presenting various types of hydrogenase and/or other enzymes. Hydrogenase is an enzyme catalyzing hydrogen formation from protons or oxidation to protons. As shown in FIG. 19A, architectural construct layers, such as single atom thick or thicker crystalline carbon 1902, 1904, 1906, 1908, 1910, 1912 illustrate the appropriately spaced pathway such as 1918 for extracting hydrogen that has been produce by the electrical neutralization of hydrogen ions from the hydrogen ion donor which may included compounds such as water or various electrolytes. Similarly graphene or thicker crystalline carbon layers parallel to planes 1902, 1904, 1906, 1908, 1910, 1912 illustrate the appropriately spaced region 1920 for producing and/or collecting and protecting various forms of hydrogenase or other enzymes and catalysts from oxidative damage.

Accordingly, electrodes constructed from an architectural construct as described herein facilitate transfer of hydrogenase and provide isolation of hydrogen to enable new processes that improve the electrode efficiency, separation efficiency, and rate of hydrogen production.

Figure 19B:
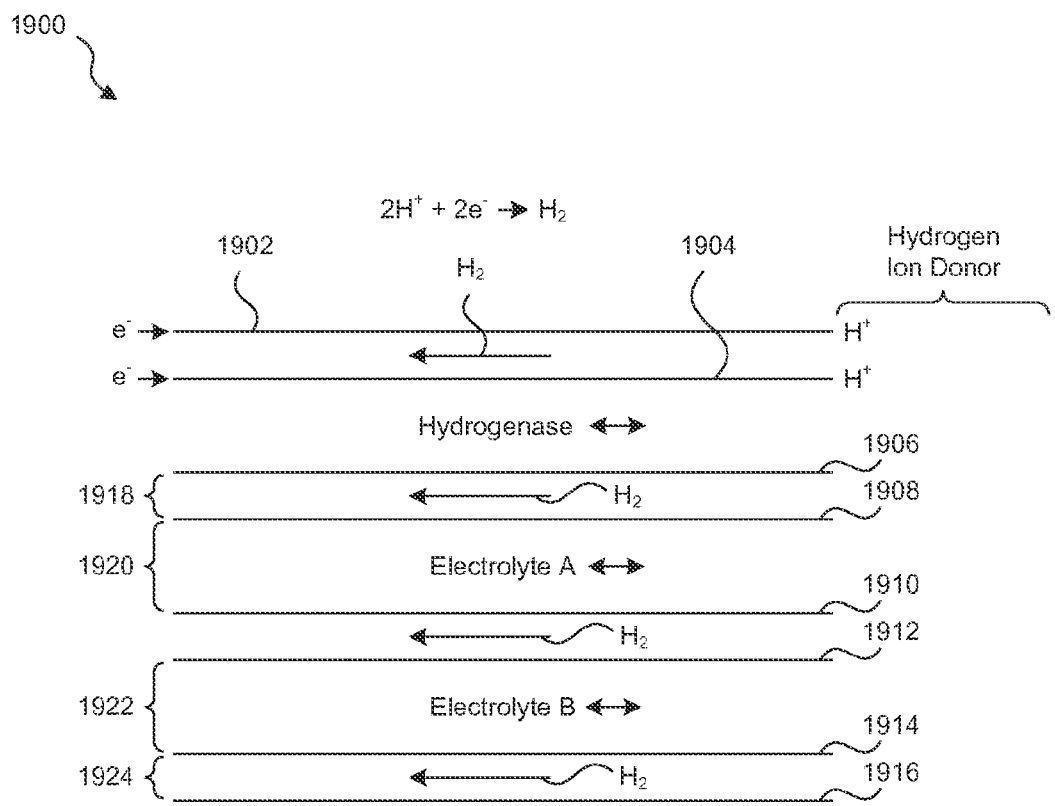

As shown further with respect to FIG. 19B, hydrogen production system 1900 utilizes architectural construct layers such as single atom thick or thicker crystalline carbon layers 1902, 1904, 1906, 1908, 1910, 1912, 1914, 1916 illustrate the appropriately spaced pathway such as 1918 for extracting hydrogen that has been produced by the electrical neutralization of hydrogen ions from the hydrogen ion donor which may be compounds such as water or various electrolytes. Similarly graphene or thicker crystalline carbon layers parallel to planes 1902, 1904, 1906, 1908, 1910, 1912, 1914, 1916 illustrate the appropriately spaced region for producing and/or collecting and protecting various forms of hydrogenase or other enzymes and catalysts from oxidative damage. According to further aspects, electrolytes such as acids or bases may also be retained in appropriate spacings 1920, 1922 as determined by the surface tension, temperature, and interrelationship with the hydrogen donor as shown. As shown in FIG. 19B, a first Electrolyte A is retained in a first spacing 1920 and a second Electrolyte B is retained in a second spacing 1922.

Figure 19C:
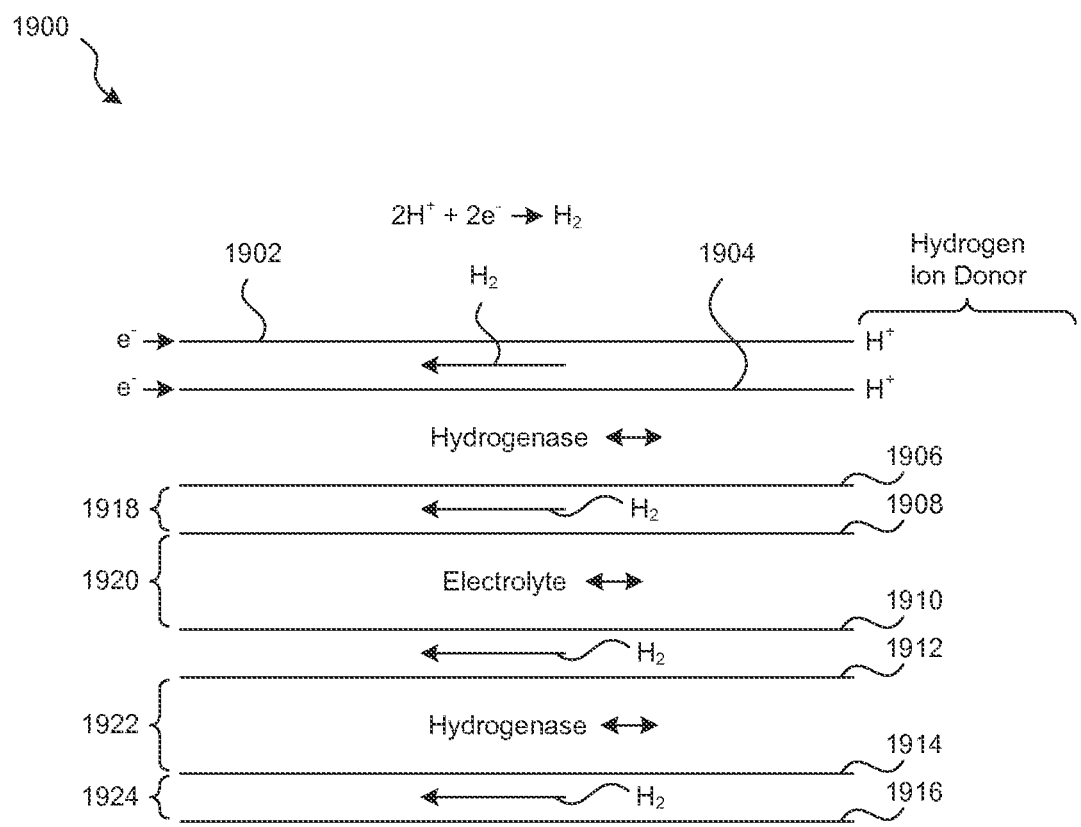

As further shown with respect to FIG. 19C, hydrogen production system 1900 includes alternating layers of contained hydrogenase and electrolyte further illustrating a configuration that allows preservation of the electrolyte, hydrogenase or other enzyme and consumption of the hydrogen ion donor.

According to still further aspects of the disclosure, solar driven oxygenic photosynthesis in which H2O is oxidized to release O2 and electrons are utilized by light-driven NADP, an electrode constructed from an architectural construct provides sufficiently rapid electron transfer to a hydrogenase, for example, an engineered protein, that is presented between appropriately spaced graphene layers and/or by the edge effect of one or more nearby layers of graphene. This provides the important advantage of extremely rapid electron transfers to intimately present hydrogenase to enable water to be directly converted into hydrogen. Similarly graphene layers intimately presenting electrons to hydrogenase can sufficiently shield the hydrogenase to provide oxygen tolerance.

According to still further aspects, solar driven purple nonsulfur bacteria produce hydrogen but require a replenishing supply of organic electron donors. An architectural construct facilitates the presentation of electrons from organic electron donors including organic materials undergoing processes such as anaerobic digestion, electrolysis or microbial fuel cell operations.

In various types of fermentive digestion, hydrogen competes with other electron sinks. An electrode constructed from an architectural construct provides numerous advantages to hydrogen production operations including:

1. Rapid isolation and removal of hydrogen upon production by presentation of electrons to hydrogen ions.
2. Improved conduction and distribution of electrons to a much larger net area than the apparent area of the architectural construct electrode.
3. Improved rate of production by expediting the presentation of hydrogen ions, hosting nucleation and/or transporting hydrogen atoms to nucleation sites, and removing diatomic hydrogen along passageways between graphene layers to prevent competitive uses of hydrogen that cause reduced net production.

Improved electrode efficiency by reduction of over-voltage, prevention of competitive consumption of hydrogen, catalytic action and protection of other catalytic agents such as hydrogenase are thus provided by electrodes and/or separators constructed of an architectural construct.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to a solar concentrator in combination with electrolytic cells and not necessarily the exemplary combinations generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all combinations that operated in accordance with the claims. Accordingly, the invention is not limited by the disclosure, but instead its scope is to be determined entirely by the following claims.

To the extent not previously incorporated herein by reference, the present application incorporates by reference in their entirety the subject matter of each of the following materials: U.S. Patent Application No. 61/237,476, filed on Aug. 27, 2009 and titled ELECTROLYZER AND ENERGY INDEPENDENCE TECHNOLOGIES; U.S. patent application Ser. No. 12/707,651, now U.S. Pat. No. 8,075,748, filed on Feb. 17, 2010 and titled ELECTROLYTIC CELL AND METHOD OF USE THEREOF; U.S. Patent Application No. 61/237,479, filed on Aug. 27, 2009 and titled FULL SPECTRUM ENERGY; U.S. Patent Application No. 61/178,442, filed on May 14, 2009 and titled ENERGY INDEPENDENCE TECHNOLOGIES; U.S. patent application Ser. No. 12/707,653, now U.S. Pat. No. 8,172,990, filed on Feb. 17, 2010 and titled APPARATUS AND METHOD FOR CONTROLLING NUCLEATION DURING ELECTROLYSIS; U.S. patent application Ser. No. 12/707,656, now U.S. Pat. No. 8,075,749, filed on Feb. 17, 2010 and titled APPARATUS AND METHOD FOR GAS CAPTURE DURING ELECTROLYSIS; U.S. patent application Ser. No. 09/969,860, now U.S. Pat. No. 6,984,305, filed on Oct. 1, 2001 and titled METHOD AND APPARATUS FOR SUSTAINABLE ENERGY AND MATERIALS; U.S. patent application Ser. No. 12/857,553, now U.S. Pat. No. 8,940,265, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES, U.S. patent application Ser. No. 12/857,541, now U.S. Pat. No. 9,231,267, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, now U.S. Pat. No. 8,808,529, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, now U.S. Pat. No. 9,097,152, filed on Aug. 16, 2010 and titled ENERGY SYSTEM FOR DWELLING SUPPORT; U.S. patent application Ser. No. 13/027,235, now U.S. Pat. No. 8,313,556, filed on Feb. 14, 2011 and titled DELIVERY SYSTEMS WITH IN-LINE SELECTIVE EXTRACTION DEVICES AND ASSOCIATED METHODS OF OPERATION; and U.S. Patent Application No.61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES.

I claim:

1. A sustainable economic development process comprising:
    extracting carbon from a carbon source using at least one of thermal dissociation and electrical dissociation;
    forming an architectural construct using the carbon, wherein the architectural construct provides a reaction zone;
    anaerobically digesting organic matter in the reaction zone; and
    collecting energy from a renewable resource, wherein said energy is at least partially received in the reaction zone, and wherein said energy that is collected is greater than the amount of energy that could have been converted by the oxidation of the carbon by means selected from the group consisting of an internal combustion engine, an external combustion engine, an electrochemical fuel cell, and a thermoelectric cell.

2. The process of claim 1 wherein the carbon source is a hydrocarbon substance, and wherein said carbon extraction includes dehydrogenation of the hydrocarbon substance to form one or more layers of the architectural construct.

3. The process of claim 1, further comprising:
    extracting pressurized hydrogen from a water-based solution containing the organic matter, wherein the reaction zone includes an anaerobic microorganism to promote production of the hydrogen from the water-based solution.

4. The process of claim 1, further comprising:
    applying the energy to the reaction zone; and
    extracting pressurized hydrogen from a water-based solution in the reaction zone, wherein the pressurized hydrogen exerts higher pressure than an initial pressure of the water-based solution.

5. The process of claim 4 wherein extracting pressurized hydrogen includes dissociating hydrogen and oxygen from the water-based solution by electrolysis.

6. The process of claim 1 wherein the architectural construct contains hydrogenase, and wherein the process further comprises:
    dissociating at least a portion of a water-based solution into at least hydrogen and another substance using said energy in the reaction zone; and
    catalyzing hydrogen production according to equation $$2H^+ + 2e^- \rightarrow H_2,$$

wherein the equation is catalyzed by the hydrogenase.

7. The process of claim 1 wherein the architectural construct includes a surface capable of enhancing growth of a microorganism.

8. The process of claim 1 wherein anaerobically digesting the organic matter in the reaction zone includes generating an electrolyte that releases hydrogen at a lower voltage than the voltage required to dissociate water.

9. The process of claim 1 wherein the renewable resource is selected from a group consisting of solar, wind, moving water, geothermal, and biomass.

10. A sustainable economic development process comprising:
   extracting carbon from a carbon source using at least one of thermal dissociation and electrical dissociation;
   forming an architectural construct using the carbon, wherein the architectural construct provides a reaction zone;
   collecting energy from a renewable resource, wherein said energy is at least partially received in the reaction zone, and wherein said energy that is collected is greater than the amount of energy that could have been converted by the oxidation of the carbon by means selected from the group consisting of an internal combustion engine, an external combustion engine, an electrochemical fuel cell, and a thermoelectric cell;
   applying said energy to the reaction zone; and
   extracting pressurized hydrogen from a water-based solution in the reaction zone.

11. The process of claim 10 wherein the pressurized hydrogen exerts higher pressure than an initial pressure of the water-based solution.

12. The process of claim 11 wherein extracting pressurized hydrogen includes dissociating hydrogen and oxygen from the water-based solution by electrolysis.

13. The process of claim 10 wherein extracting pressurized hydrogen includes dissociating hydrogen and oxygen from the water-based solution by electrolysis.

14. The process of claim 10 wherein the renewable resource is selected from a group consisting of solar, wind, moving water, geothermal, and biomass.

15. A sustainable economic development process comprising:
   extracting carbon from a carbon source using at least one of thermal dissociation and electrical dissociation;
   forming an architectural construct using the carbon, wherein the architectural construct provides a reaction zone, and wherein the architectural construct contains hydrogenase;
   collecting energy from a renewable resource, wherein said energy is at least partially received in the reaction zone, and wherein said energy that is collected is greater than the amount of energy that could have been converted by the oxidation of the carbon by means selected from the group consisting of an internal combustion engine, an external combustion engine, an electrochemical fuel cell, and a thermoelectric cell; and
   dissociating at least a portion of a water-based solution into at least hydrogen and another substance using said energy in the reaction zone.

16. The process of claim 15 further comprising catalyzing hydrogen production according to equation $$2H^+ + 2e^- \rightarrow H_2,$$

wherein the equation is catalyzed by the hydrogenase.

17. The process of claim 15 wherein the renewable resource is selected from a group consisting of solar, wind, moving water, geothermal, and biomass.

* * * * *